(12) United States Patent
Long

(10) Patent No.: US 8,216,234 B2
(45) Date of Patent: Jul. 10, 2012

(54) TISSUE RESECTION DEVICE

(75) Inventor: Gary L. Long, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1797 days.

(21) Appl. No.: 10/986,602

(22) Filed: Nov. 10, 2004

(65) Prior Publication Data

US 2006/0100614 A1 May 11, 2006

(51) Int. Cl.
*A61B 18/14* (2006.01)
(52) U.S. Cl. .......................................... 606/50; 606/47
(58) Field of Classification Search ............... 606/41, 606/45–50, 113, 114
See application file for complete search history.

(56) References Cited

U.S. PATENT DOCUMENTS

| | | | | |
|---|---|---|---|---|
| 4,524,770 A * | 6/1985 | Orandi | | 606/46 |
| 5,336,222 A * | 8/1994 | Durgin et al. | | 606/50 |
| 5,336,227 A | 8/1994 | Nakao et al. | | |
| 5,403,311 A * | 4/1995 | Abele et al. | | 606/49 |
| 5,458,597 A * | 10/1995 | Edwards et al. | | 606/41 |
| 5,535,759 A * | 7/1996 | Wilk | | 128/898 |
| 5,536,267 A * | 7/1996 | Edwards et al. | | 606/41 |
| 5,741,271 A * | 4/1998 | Nakao et al. | | 606/114 |
| 5,846,248 A | 12/1998 | Chu et al. | | |
| 5,897,554 A * | 4/1999 | Chia et al. | | 606/41 |
| 5,947,978 A | 9/1999 | Holsinger | | |
| 5,961,526 A | 10/1999 | Chu et al. | | |
| 6,007,546 A * | 12/1999 | Snow et al. | | 606/113 |
| 6,123,665 A * | 9/2000 | Kawano | | 600/104 |
| 6,210,416 B1 | 4/2001 | Chu et al. | | |
| 6,371,963 B1 * | 4/2002 | Nishtala et al. | | 606/113 |
| 6,610,056 B2 * | 8/2003 | Durgin et al. | | 606/41 |

FOREIGN PATENT DOCUMENTS

| | | |
|---|---|---|
| DE | 87 11 635 U1 | 1/1988 |
| DE | 97 11 635 U1 | 1/1988 |
| JP | O9-173348 | 7/1997 |
| JP | 11-503631 | 3/1999 |

* cited by examiner

*Primary Examiner* — Michael Peffley

(57) ABSTRACT

A medical device for performing a therapeutic procedure on a patient. The medical device includes an elongate probe extending to an applicator end sized and shaped to be slidably received in an endoscope working channel. The device also includes an injection needle positioned adjacent the applicator end of the probe. The injection needle is communicatible with a fluid source for delivering fluid and an electrical energy source for delivering electrical energy to the needle when performing the therapeutic procedure on the patient. The needle also has a central axis. The device further includes an ablating loop positioned adjacent the applicator end of the probe. The ablating loop is communicatible with the electrical energy source for delivering electrical energy to the ablating loop when performing the therapeutic procedure. The ablating loop also has a central axis that is spaced from the central axis of the injection needle. During operation of the device, the injection needle and ablating loop have opposite charges for ablating tissue of the patient.

23 Claims, 32 Drawing Sheets

TISSUE RESECTION DEVICE

FIELD OF INVENTION

The present invention relates to a medical device, and more particularly to an ablation and resection device for performing therapy on a patient therewith.

BACKGROUND OF THE INVENTION

Various devices and methods have been traditionally used to ablate or remove unwanted polyps, tumors, lesions, and similar abnormal growths located within a patient cavity. An example of such abnormal growths is pre-cancerous polyps or tumors that commonly develop in the glands and cells that line the colon and rectum. Other examples of abnormal growths include polypoid lesions or esophageal squamous papilloma, which are rare benign tumors of the upper gastrointestinal tract, and neoplasms of the esophagus. If not removed or destroyed, such abnormal growths often advance to more severe stages and create complications in the patient. For example, malignant tumors may spread within the body beyond their original location and create life threatening conditions.

Common methods for treating abnormal intracavital growths include resection, cryotherapy, and thermal therapy. Resection, also known as excision, is the cutting of unwanted growth from the patient. For resection methods that include capture of the tissue cut away from the patient, benefits include the patient being immediately free of the unwanted tissue and the ability to analyze the removed tissue in the laboratory. Cryotherapy, also known as cryoablation, is the application of extreme cold to freeze and destroy unwanted tissue. For example, liquid nitrogen or liquid argon are used to supercool probes used to freeze unwanted tissue. Thermal therapy, also known as thermal ablation and heat ablation, is the application of heat to coagulate, cauterize and/or ablate diseased mucosal tissue. The most common form of thermal ablation is radiofrequency ablation where radiofrequency energy is applied to the unwanted tissue. Other heat therapies include microwave coagulonecrotic therapy, laser therapy, and high intensity focused ultrasound. In cryotherapy and thermal therapy, sufficient raising or lowering of tissue temperature, respectively causes necrosis of the effected tissue. For convenience, the term ablate will be used herein to describe any and all of these thermal therapy processes. In use, these devices are placed adjacent the unwanted tissue and tissue is ablated, cauterized, coagulated, frozen, or burnt, as the case may be, by energy transmitted from or to the device.

Traditional treatment devices have three primary shortcomings. First, traditional devices can ablate or resect only relatively small portions of patient tissue at one time. For example, ablation devices having a surface for ablating patient tissue by transmitting energy to or from the surface can only ablate an area of patient tissue substantially equal to the area of the transmission surface in a single energy transmission.

A second primary shortcoming of traditional treatment devices is their inaccuracy in use. A primary challenge for treating unwanted growths is to destroy or resect the targeted tissue without adversely affecting healthy adjacent or underlying cells. Regarding ablation devices especially, damage to healthy underlying esophageal muscle tissue often leads to the creation of a stricture or constriction in the esophagus. Many traditional ablation devices ablate targeted tissue without first isolating the targeted tissue from adjacent and underlying healthy tissue. As a result, when too much energy is transferred to or from the device, ablation of healthy adjacent cells and/or underlying cells can occur. On the other hand, when too little energy is transferred from the device, less than all of the targeted tissue is treated.

A third primary shortcoming of traditional devices is present with devices having resecting capability. Use of conventional resection devices allows for resection of tissue from a patient, but leaves non-cauterized, or insufficiently cauterized tissue in the patient. Non-cauterized or insufficiently cauterized tissue remaining in the patient after a resection may lead to infection or bleeding.

The conventional approaches for treating unwanted and abnormal growths requiring the precise resection and/or ablation of relatively large portions of intralumenal tissue are insufficient in these regards. Thus, there is a need for a resection and ablation device and a method for using such a device that allow accurate and minimally invasive resection and ablation, as the case may be, of relatively large amounts of intralumenal patient tissue.

BRIEF SUMMARY OF THE INVENTION

The present invention relates to a medical device for performing a therapeutic procedure on a patient. The medical device has an elongate probe extending to an applicator end sized and shaped to be slidably received in an endoscope working channel. The device also includes an injection needle positioned adjacent the applicator end of the probe. The injection needle is communicatible with a fluid source for delivering fluid and an electrical energy source for delivering electrical energy to the needle when performing the therapeutic procedure on the patient. The needle also has a central axis. The device further includes an ablating loop positioned adjacent the applicator end of the probe. The ablating loop is communicatible with the electrical energy source for delivering electrical energy to the ablating loop when performing the therapeutic procedure. The ablating loop also has a central axis that is spaced from the central axis of the injection needle. During operation of the device, the injection needle and ablating loop have opposite charges for ablating tissue of the patient.

In another aspect, the present invention includes a medical device for performing a procedure on a patient. The devices has an elongate endoscope extending to a working end. The endoscope has optics for viewing an object positioned in a viewing area adjacent the working end and a working channel extending along the endoscope to a port adjacent the working end. The device also includes an elongate probe slidably disposed in the working channel. The elongate probe has an applicator end corresponding to the working end of the endoscope. The device further includes an injection needle positioned adjacent the applicator end of the probe in the viewing area. The injection needle has a central axis and is communicatible with a fluid source for delivering fluid to the needle and an electrical energy source for delivering electrical energy to the needle when performing the therapeutic procedure on the patient. The device further includes an ablating loop positioned adjacent the applicator end of the probe in the viewing area. The ablating loop is communicatible with the electrical energy source for delivering electrical energy to the ablating loop when performing the therapeutic procedure. The ablating loop has a central axis that is spaced from the central axis of the injection needle. During operation of the device, the injection needle and ablating loop have opposite charges for ablating tissue of the patient.

In yet another aspect, the present invention includes a method for performing a procedure on a patient. The method includes guiding a working end of an endoscope to a predetermined location within the patient. The method also includes positioning an ablating loop having a central axis and an injection needle having a central axis adjacent the working end of the endoscope such that the central axis of the ablating loop is spaced from the central axis of the injection needle. The method further includes injecting fluid through the injection needle into tissue of the patient adjacent the predetermined location within the patient. In addition, the method includes applying electrical energy to the injection needle and ablating loop simultaneously such that the injection needle and ablating loop have opposite charges, thereby ablating at least a portion of the tissue.

In still another aspect, the present invention includes a method for performing a procedure on a patient. The method includes guiding a working end of an endoscope to a predetermined location within the patient. The method also includes positioning a cutting loop, an injection needle, a retainer, and an ablating loop adjacent the working end of the endoscope. The method further includes injecting fluid through the injection needle into tissue of the patient adjacent the predetermined location within the patient and cutting at least a portion of the tissue from the patient. In addition, the method includes capturing the tissue cut from the patient in the cutting step with the retainer and applying energy to the ablating loop thereby ablating tissue remaining in the patient after the cutting step.

In yet still another aspect, the present invention includes a medical device for performing a procedure on a patient. The device includes an elongate endoscope extending to a working end having an exterior surface and having optics for viewing an object positioned in a viewing area adjacent the working end. The device also includes an elongate probe connected to the exterior surface of the endoscope and having an applicator end corresponding to the working end of the endoscope. The device further includes an injection needle positioned adjacent the applicator end of the probe in the viewing area and communicatible with a fluid source for delivering fluid to the needle and an electrical energy source for delivering electrical energy to the needle when performing the therapeutic procedure on the patient. The device yet further includes an ablating loop positioned adjacent the applicator end of the probe in the viewing area and communicatible with the electrical energy source for delivering electrical energy to the ablating loop when performing the therapeutic procedure.

In a further aspect, the present invention includes a method for performing a procedure on a patient. The method includes guiding a working end of an endoscope having an elongate probe connected to an exterior surface of the endoscope adjacent the working end to a predetermined location within the patient. The method also includes positioning an ablating loop and an injection needle adjacent an application end of the probe corresponding to the working end of the endoscope. The method further includes injecting fluid through the injection needle into tissue of the patient adjacent the predetermined location within the patient. The method yet further includes applying electrical energy to the injection needle and ablating loop simultaneously such that the injection needle and ablating loop have opposite charges, thereby ablating at least a portion of the tissue.

Other aspects of the present invention will be in part apparent and in part pointed out hereinafter.

BRIEF DESCRIPTION OF THE FIGURES

Corresponding reference characters indicate corresponding parts throughout the several views of the drawings.

DETAILED DESCRIPTION OF THE INVENTION

Figure 1:
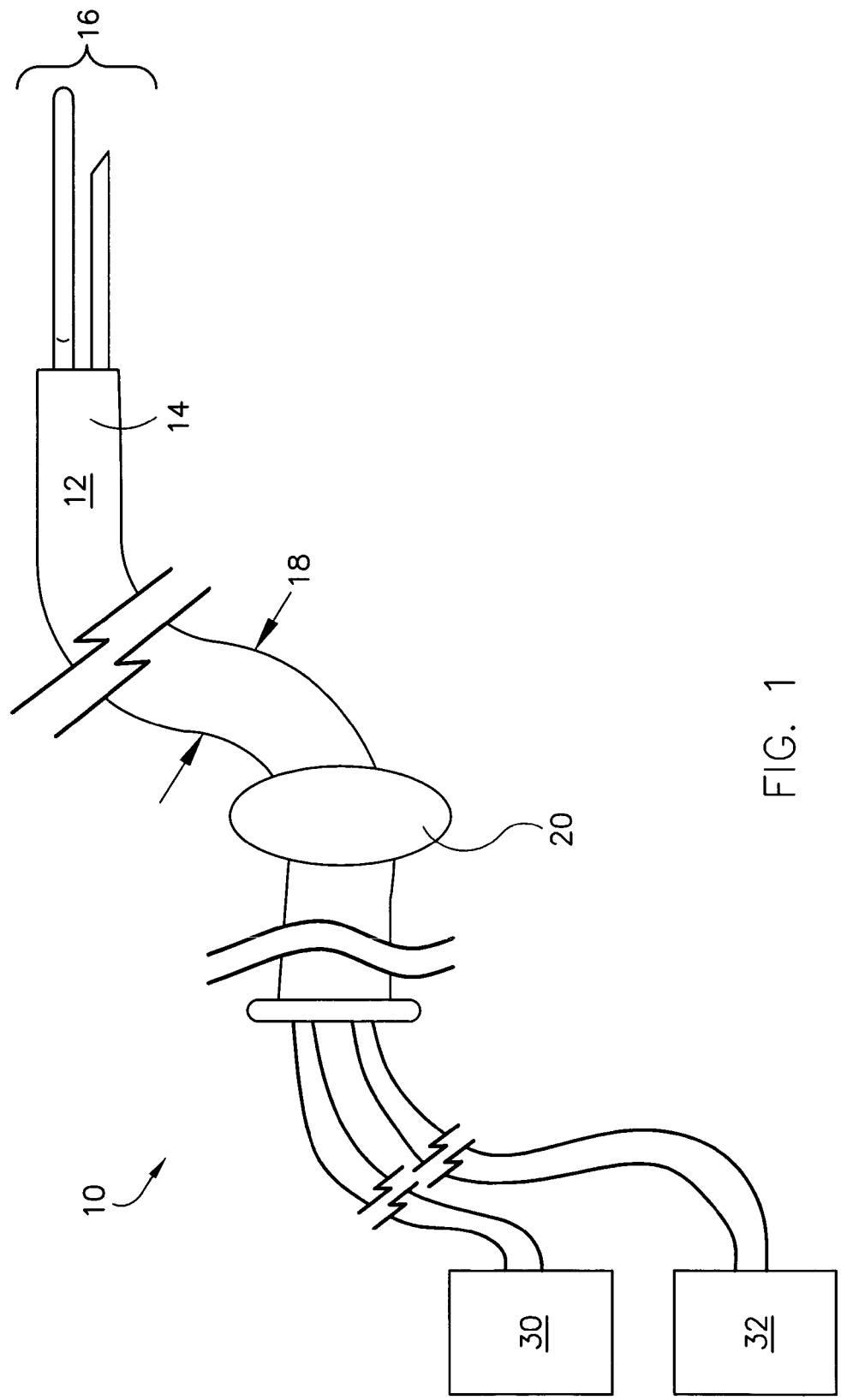
FIG. 1 is a perspective of a first embodiment of a medical device according to the present invention.

The present invention relates to a medical device for performing a therapeutic procedure on a patient, and more particularly a medical device for ablating and resecting unwanted tissue at a predetermined location within a patient. Referring now to the figures, and more particularly to FIG. 1, a medical device according to a first embodiment of the present invention is designated in its entirety by reference number 10. The medical device 10 has an elongate probe 12 extending to an applicator end 14. Applicator elements 16 are connected to the probe 12 adjacent the applicator end 14 of the probe. Although the probe may be made of other materials without departing from the scope of the present invention, in one embodiment the probe 12 is made of a flexible and thermally and/or electrically insulating material, such as silicone, polyethylene, or polypropylene. Although the probe may have other shapes without departing from the scope of the present invention, in one embodiment the probe 12 is generally tubular. Further, although the probe may have other dimensions without departing from the scope of the present invention, in one embodiment the probe 12 has a maximum width 18 of between about 1 millimeter and about 5 millimeters. Having a maximum width 18 less than about 3 millimeters allows the probe 12 to fit inside the working channel of a standard endoscope (not shown in FIGS. 1-12). The probe may have one or more traction elements 20, which increase the ability of a user to control the device 10.

Figure 2:
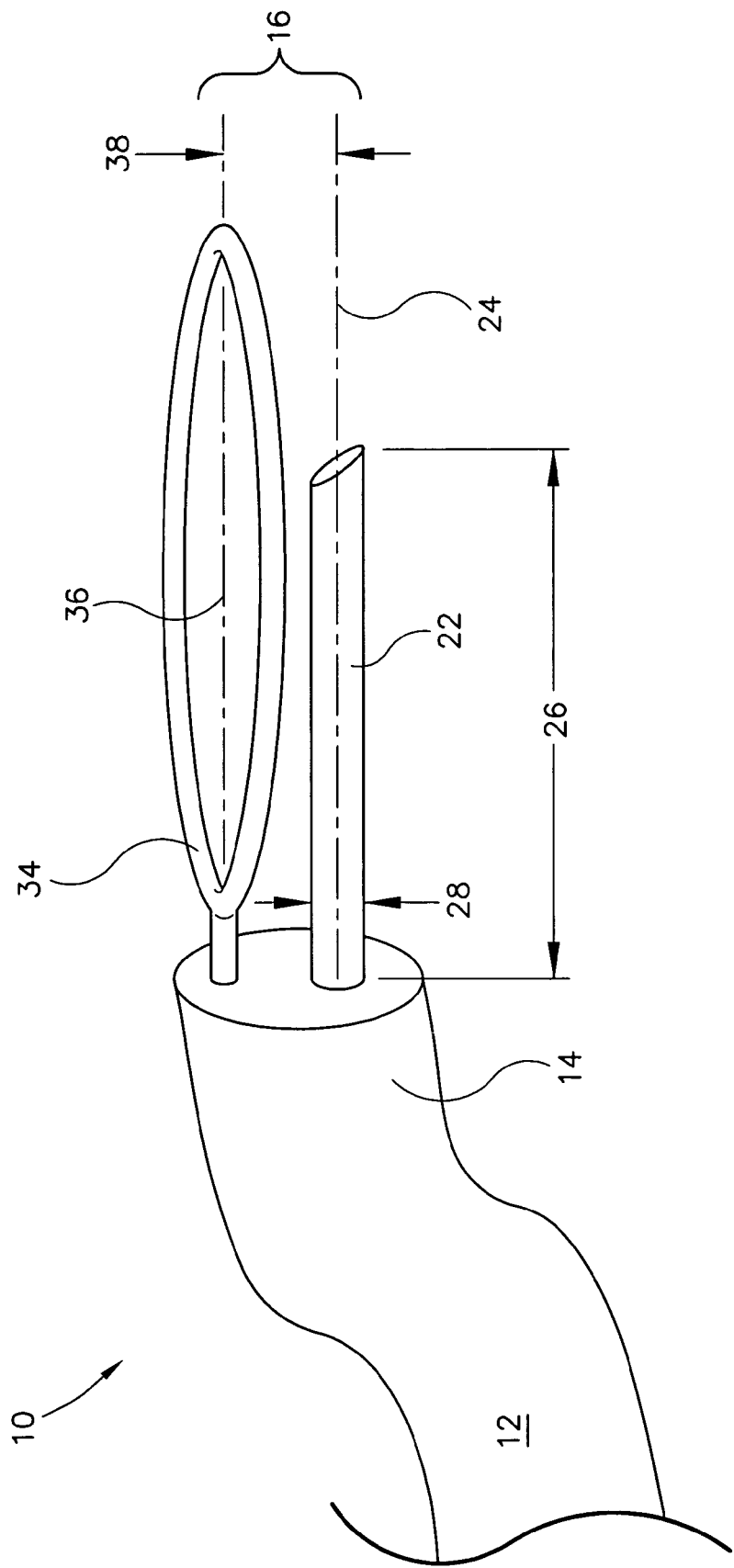
FIG. 2 is a perspective of a portion of the device shown in FIG. 1.
Figure 3:
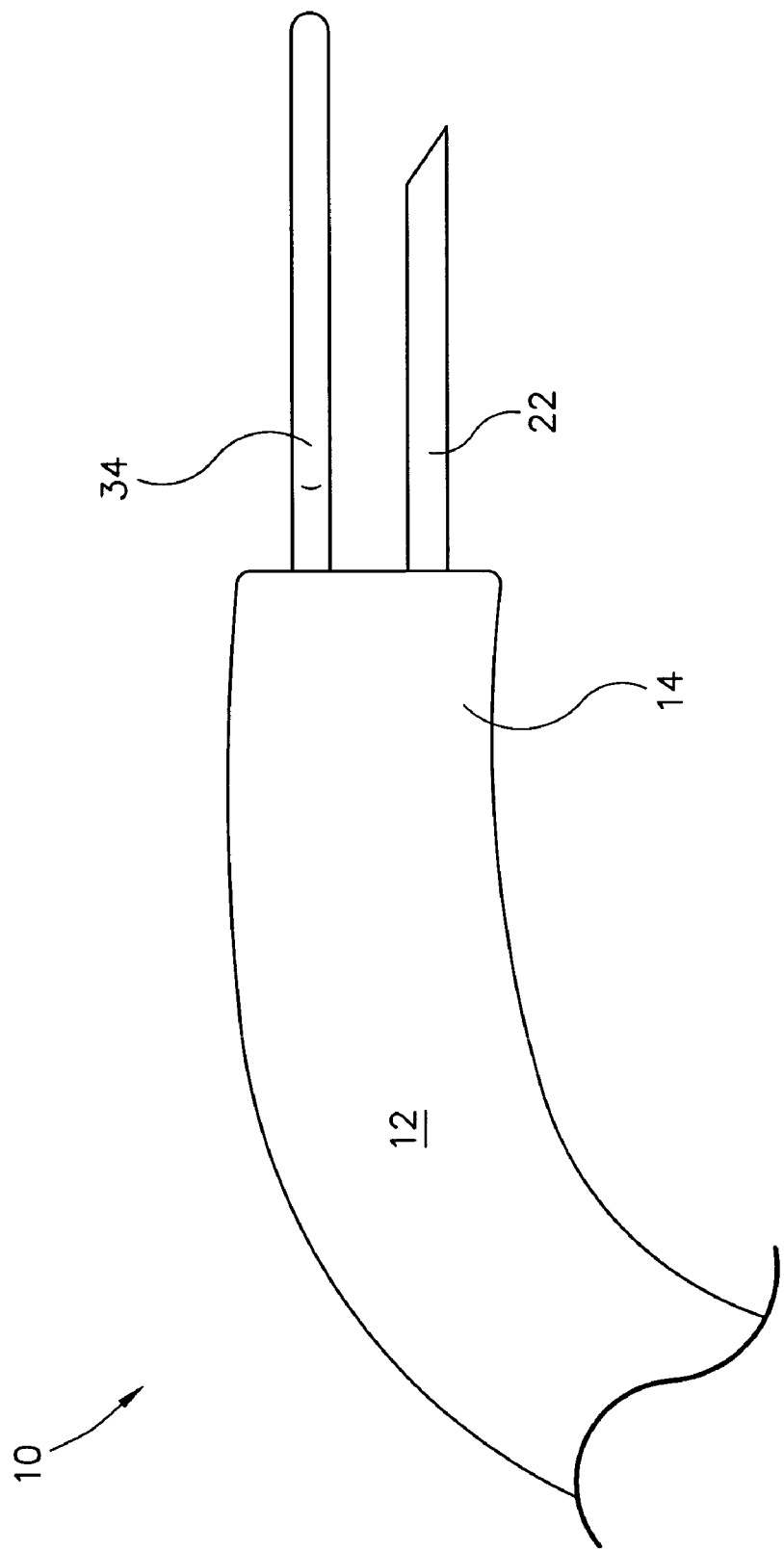
FIG. 3 is a side view of the device shown in FIG. 1.

As shown in FIG. 2, the applicator elements 16 include an injection needle 22 connected to the probe 12 adjacent the applicator end 14 of the probe. The needle 22 extends away from the probe 12 along a central axis 24. Although the needle may have other dimensions without departing from the scope of the present invention, in one embodiment the needle 22 has a maximum length 26 of between about 10 millimeters and about 20 millimeters and an outer diameter 28 of between about 0.5 millimeters and about 2 millimeters. Also, although the needle may be made of other materials without departing from the scope of the present invention, in one embodiment the needle 22 is made of any material traditionally used to make medical needles, such as 23 gage stainless steel. Further, although the needle 22 is shown as being substantially straight, the needle may have other shapes without departing from the scope of the invention. For example, in one alternate embodiment the needle may be curved (not shown).

The needle 22 is communicatible with an energy source 30, as shown in FIG. 1. The energy source 30 delivers energy to the needle 22 during the therapeutic procedure. Although other energy sources may be used without departing from the scope of the present invention, in one embodiment the energy source 30 is an electrical generator for delivering electrical current to the needle 22. Although such an electrical generator may produce electrical current having other characteristics without departing from the scope of the present invention, in one embodiment it produces a current having a voltage of between about 10 volts and about 500 volts and a frequency of between about 0.3 megahertz and about 1.0 megahertz. In another embodiment, the energy source 30 is a radio frequency generator for delivering radio frequency energy to the needle 22. Although such a radio frequency generator may produce signals having other characteristics without departing from the scope of the present invention, in one embodiment the radio frequency generator produces a signal having an amplitude of between about 10 volts and about 500 volts and a frequency of between about 0.3 megahertz and about 1.0 megahertz. In yet another embodiment, the energy source 30 delivers ultrasonic energy to the injection needle 22. Although such an ultrasonic generator may produce signals having other frequencies without departing from the scope of the present invention, in one embodiment the ultrasonic generator produces a signal having a frequency of between about 10 kilohertz and about 100 kilohertz.

The needle 22 also communicates with a fluid source 32, as shown in FIG. 1. The fluid source 32 delivers an electrically conductive fluid to the needle 22 during the therapeutic procedure. Although other fluid sources may be used without departing from the scope of the present invention, in one embodiment the fluid source 32 is a conventional saline source for delivering saline to the needle 22. Alternatively, the fluid source 32 may be a sclerotherapy agent (e.g., absolute ethanol) source for delivering sclerotherapy agent, such as absolute ethanol commonly used in hospitals, to the needle 22.

Figure 4:
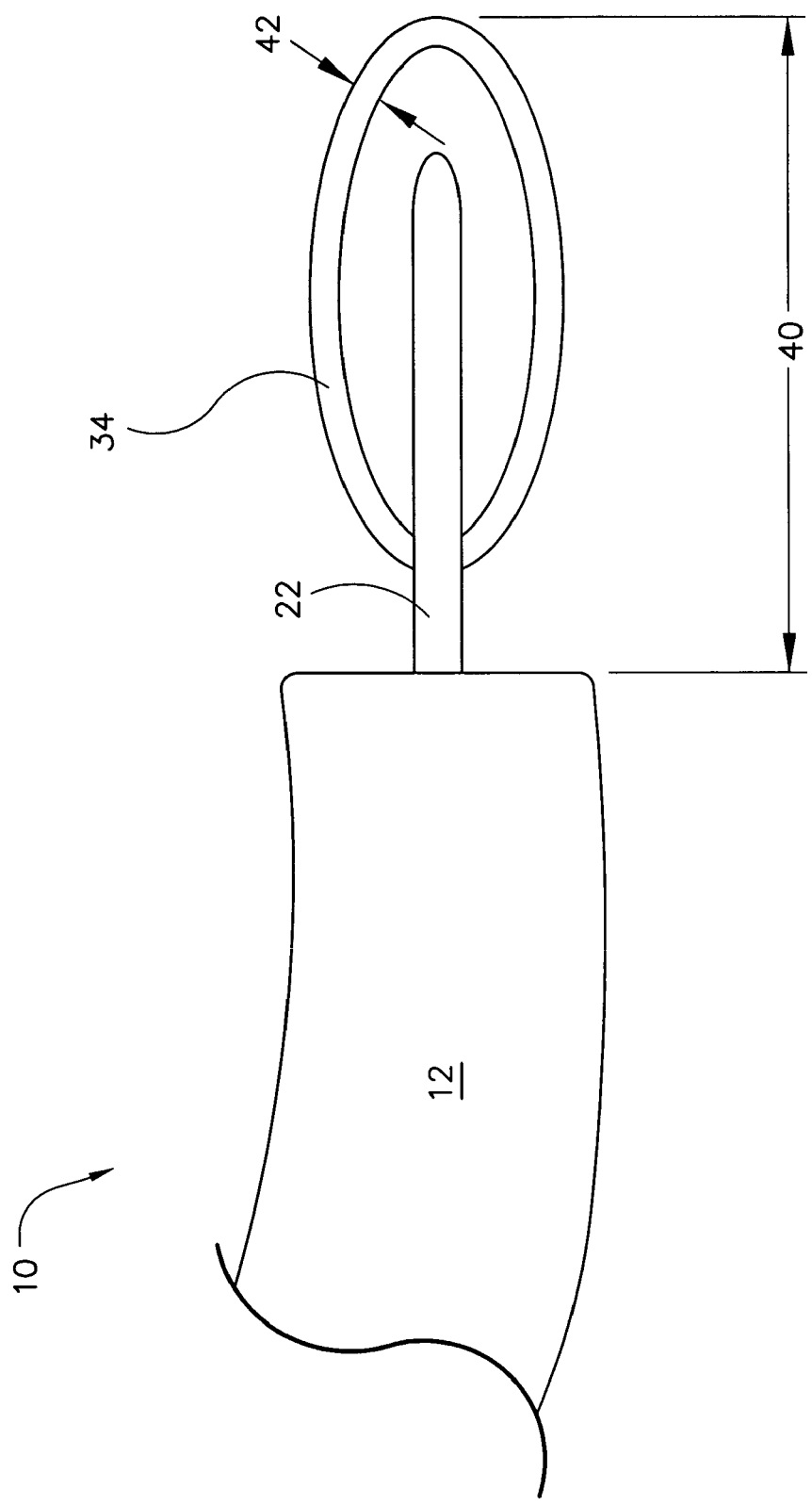
FIG. 4 is a bottom plan of the device shown in FIG. 1.
Figure 5:
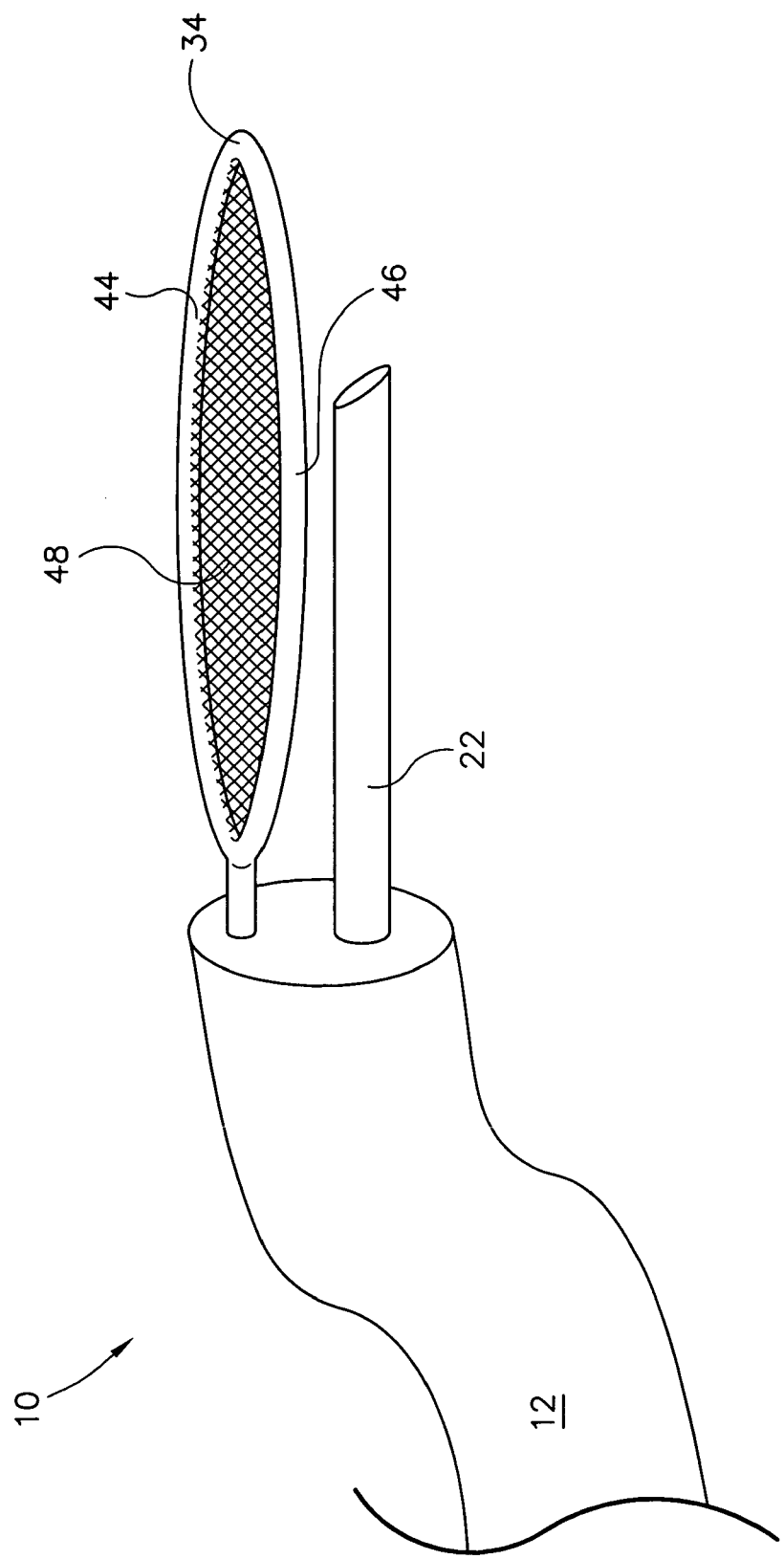
FIG. 5 is a perspective of a device similar to that shown in FIG. 2 but having a mesh extending across the loop.

The applicator elements 16 also include an ablating loop 34 positioned adjacent the applicator end 14 of the probe 12. The ablating loop 34 extends away from the probe 12 along a central axis 36. Although the central axis 24 of the needle 22 and the central axis 36 of the ablating loop 34 may be spaced by other distances without departing from the scope of the present invention, in one embodiment the axes are spaced by a distance 38 of between about 2 millimeters and about 5 millimeters. As shown in FIG. 4, the ablating loop 34 and the needle 22 are substantially centered about the horizontal center of the probe 12. Although the ablating loop 34 may have other dimensions without departing from the scope of the present invention, in one embodiment the ablating loop 34 has a length 40 of between about 10 millimeters and about 30 millimeters and a diameter 42 of between about 0.5 millimeters and about 1.5 millimeters. Further, although the ablating loop may be made of other materials without departing from the scope of the present invention, in one embodiment the ablating loop 34 is made of nitinol. The ablating loop 34 may include a conductive material positioned between sides 44, 46 of the loop forming a net or fine mesh 48, as shown in FIG. 5. Although the mesh may be made of other materials without departing from the scope of the present invention, in one embodiment the mesh 48 is made of stainless steel. The mesh 48 ensures that the energy applied to the target tissue (not shown in FIGS. 1-14) from the ablating loop 34 is more evenly distributed about the target tissue. The ablating loop 34 may be shaped to facilitate connection with the mesh 48. For example, the ablating loop 34 can include hooks or openings (not shown) for connecting the mesh 48 to the loop. Alternatively, the ablating loop 34 and mesh 50 can be fabricated together as one piece. The ablating loop 34 is also connected to the energy source 30 for delivering energy to the ablating loop during the therapeutic procedure.

In one embodiment of the present invention, the injection needle 22 and the ablating loop 34 have opposite polarities when the medical device 10 is in use. For example, with either the radio frequency or the electrical power generators 30, the needle 22 can have a charge opposite the charge of the ablating loop 34. Such bipolar energy transmission is generally safer than mono-polar energy applications which can create coagulation zones that are too deep. Also, the characteristics of the needle 22 and the ablating loop 34 may change. That is, the characteristics for the needle 22 and ablating loop 34 may alternate or otherwise change with time during use of the medical instrument 10. Such varying signal characteristics, or multiplexing, results in higher levels of energy concentrated at and delivered from the needle 22 and ablating loop 34 as a result of the interaction of differing signals between the needle and ablating loop.

Figure 6:
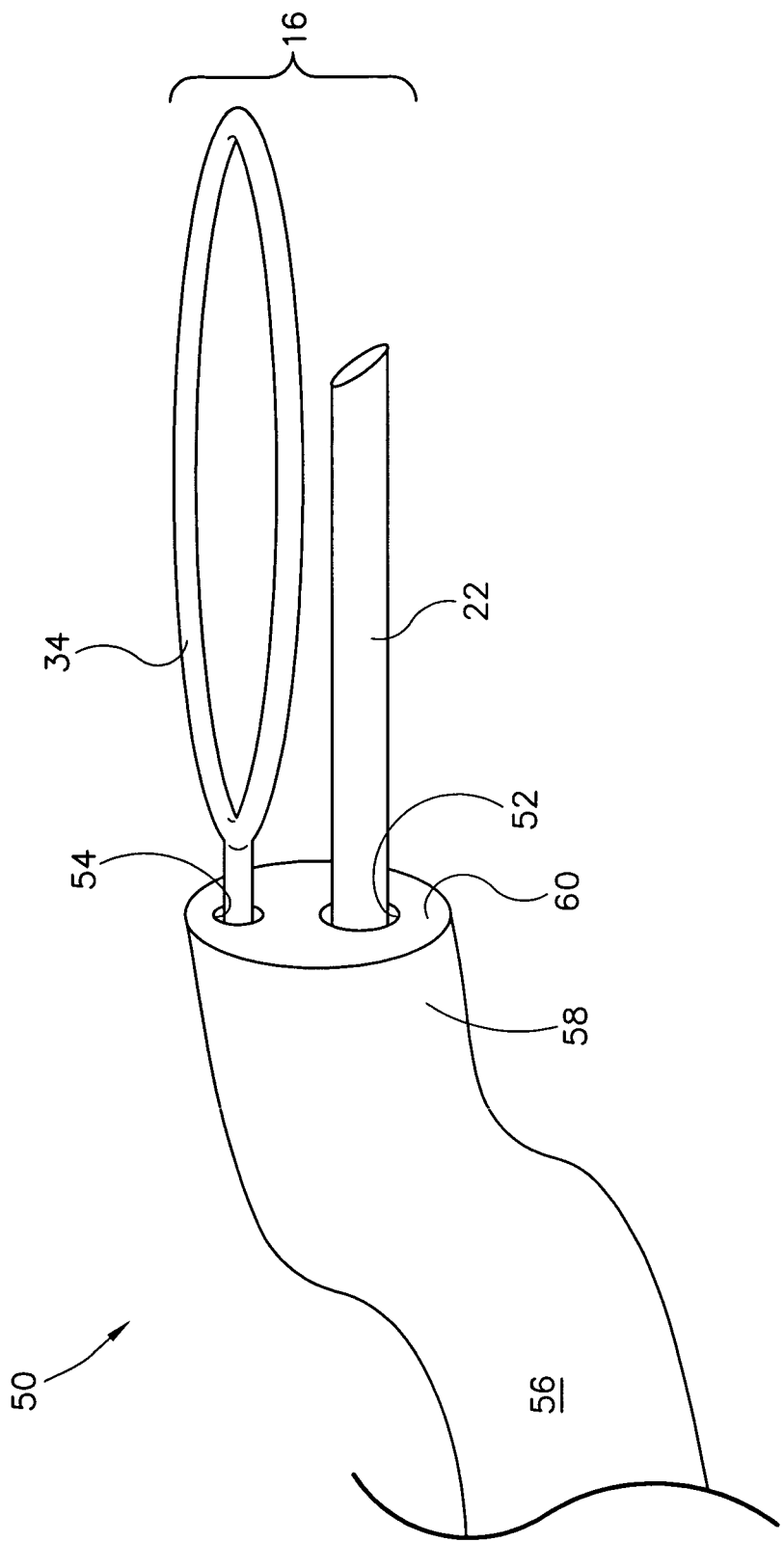
FIG. 6 is a perspective of a second embodiment of a medical device according to the present invention.
Figure 7:
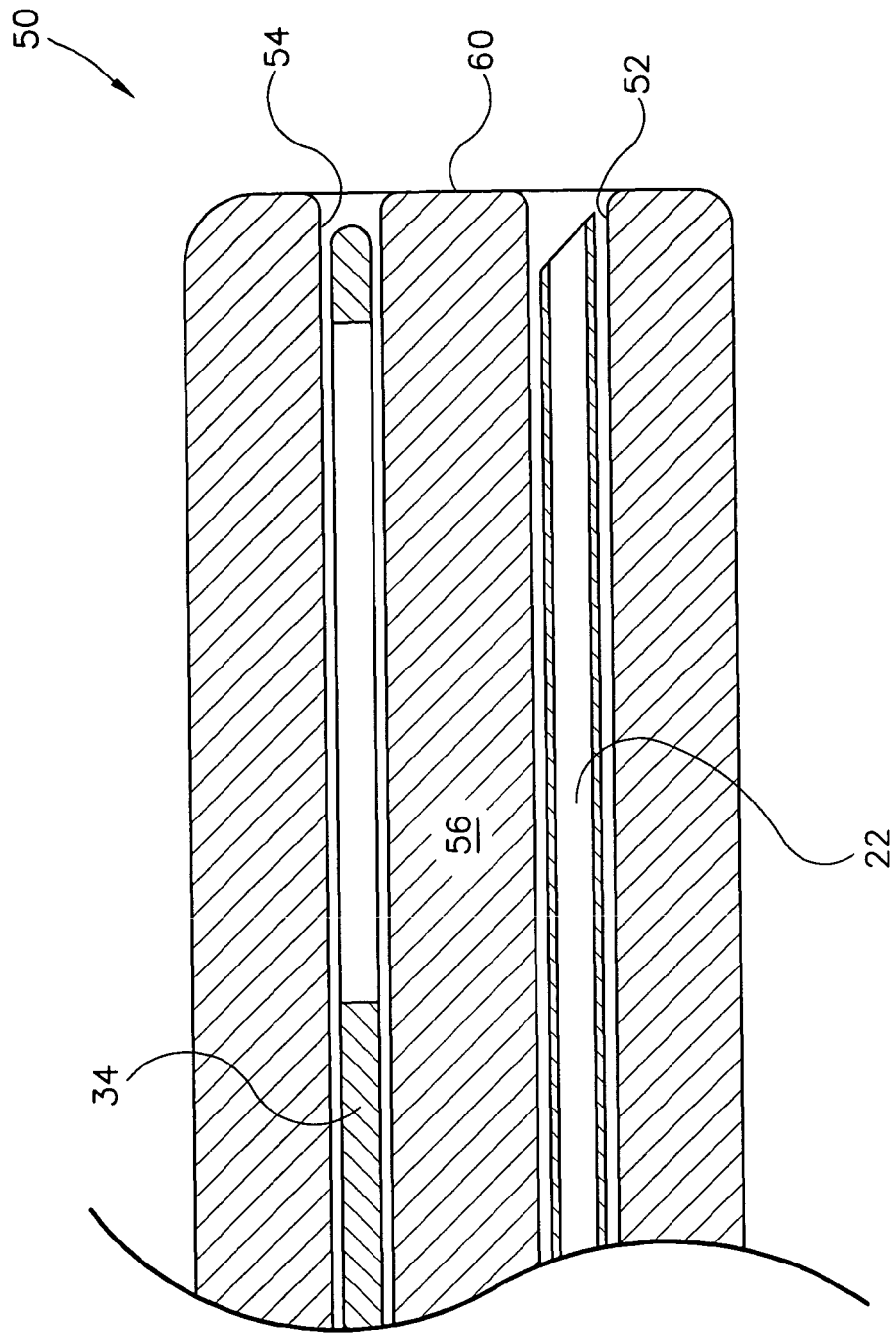
FIG. 7 is a cross-sectional side elevation of the embodiment of the medical device shown in FIG. 6 having a stored needle and ablating loop.
Figure 8:
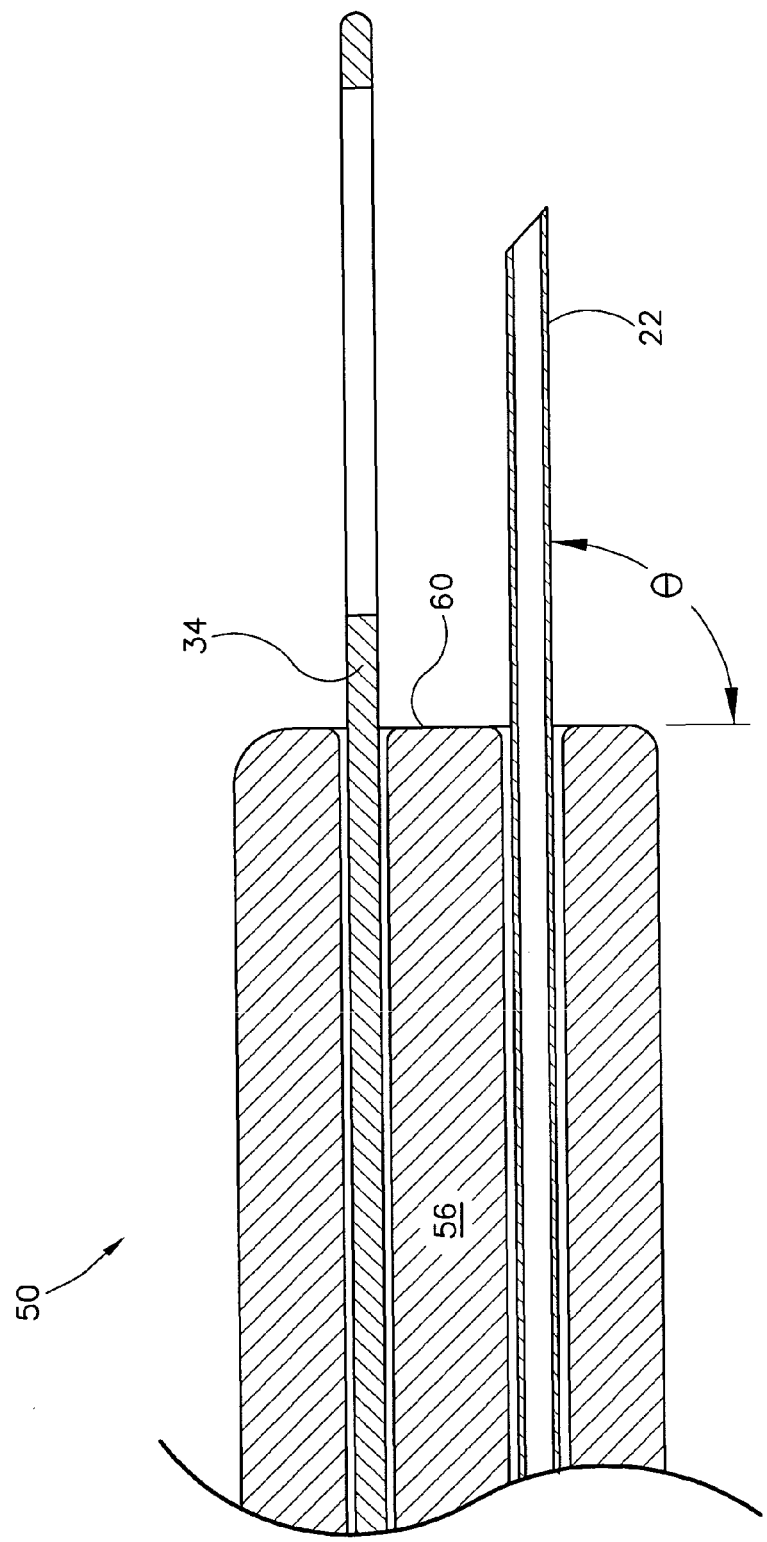
FIG. 8 is a cross-sectional side elevation of the embodiment of the medical device shown in FIG. 6 having a deployed needle and ablating loop.

FIGS. 6-8 show a second embodiment of a medical device 50 according to the present invention in which the injection needle 22 and ablating loop 34 are slidably disposed within respective channels 52, 54 of the elongate probe 56. In this embodiment, the needle 22 and the ablating loop 34 can be moved between multiple positions. For example, FIG. 7 shows the needle 22 and ablating loop 34 in stored positions in which the needle and ablating loop are recessed in the probe 56. FIG. 8 shows the needle 22 and ablating loop 34 in deployed positions in which the needle and ablating loop extend beyond the face 60 of the applicator end 58 of the probe 56. The needle 22 extends out of the probe 56 at an angle θ with the face 60 of the applicator end 58 of the probe. Although FIG. 8 shows an angle θ of approximately 90 degrees, the needle may extend from the probe face at other angles without departing from the scope of the present invention. For example, the needle 22 may move out of the probe at an angle θ of between about 60 degrees and about 90 degrees. The needle 22 and ablating loop 34 are otherwise identical to the needle and ablating loop of the first embodiment, and therefore will not be described in further detail.

Figure 9:
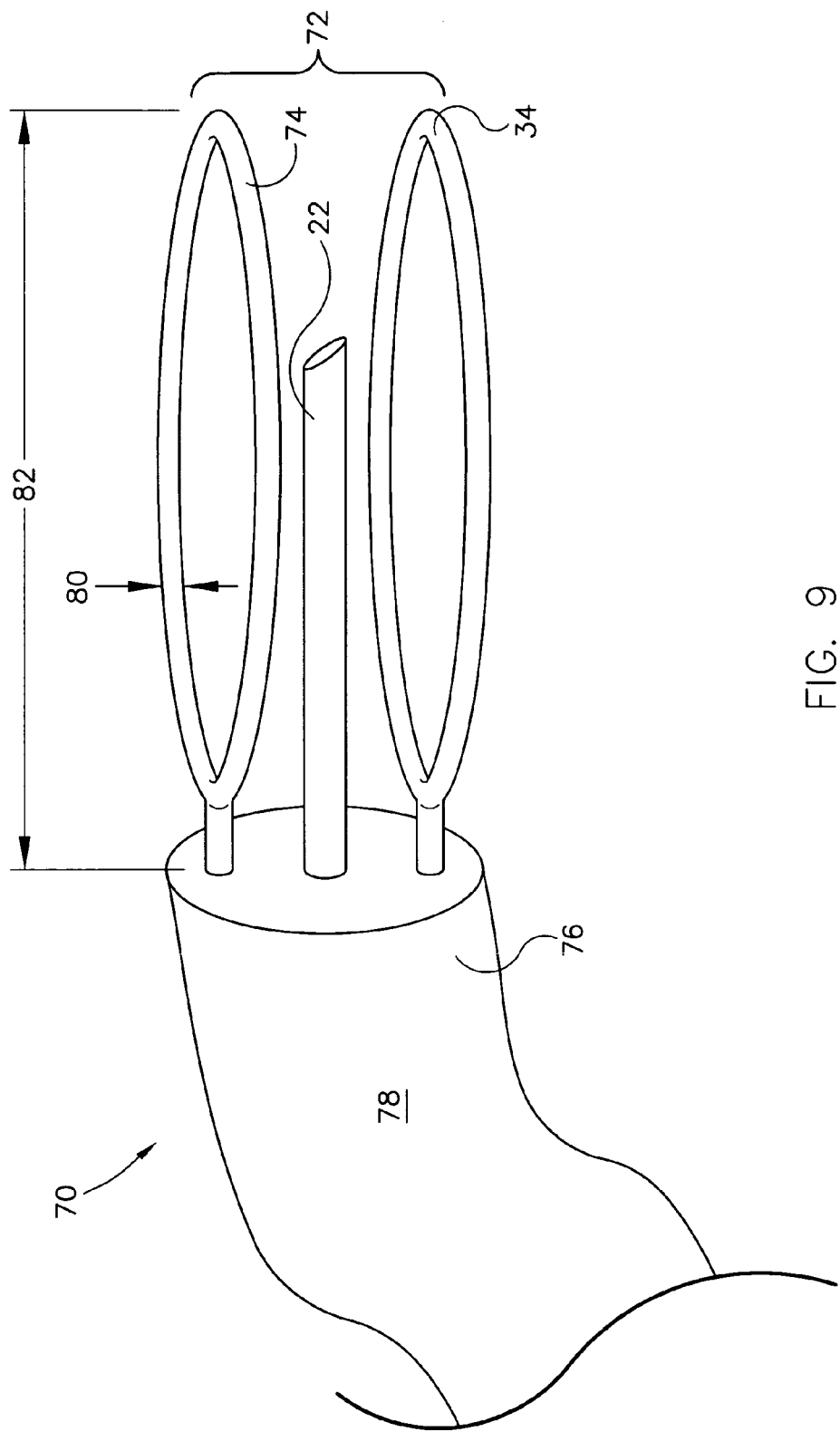
FIG. 9 is a perspective of a third embodiment of a medical device according to the present invention.
Figure 10:
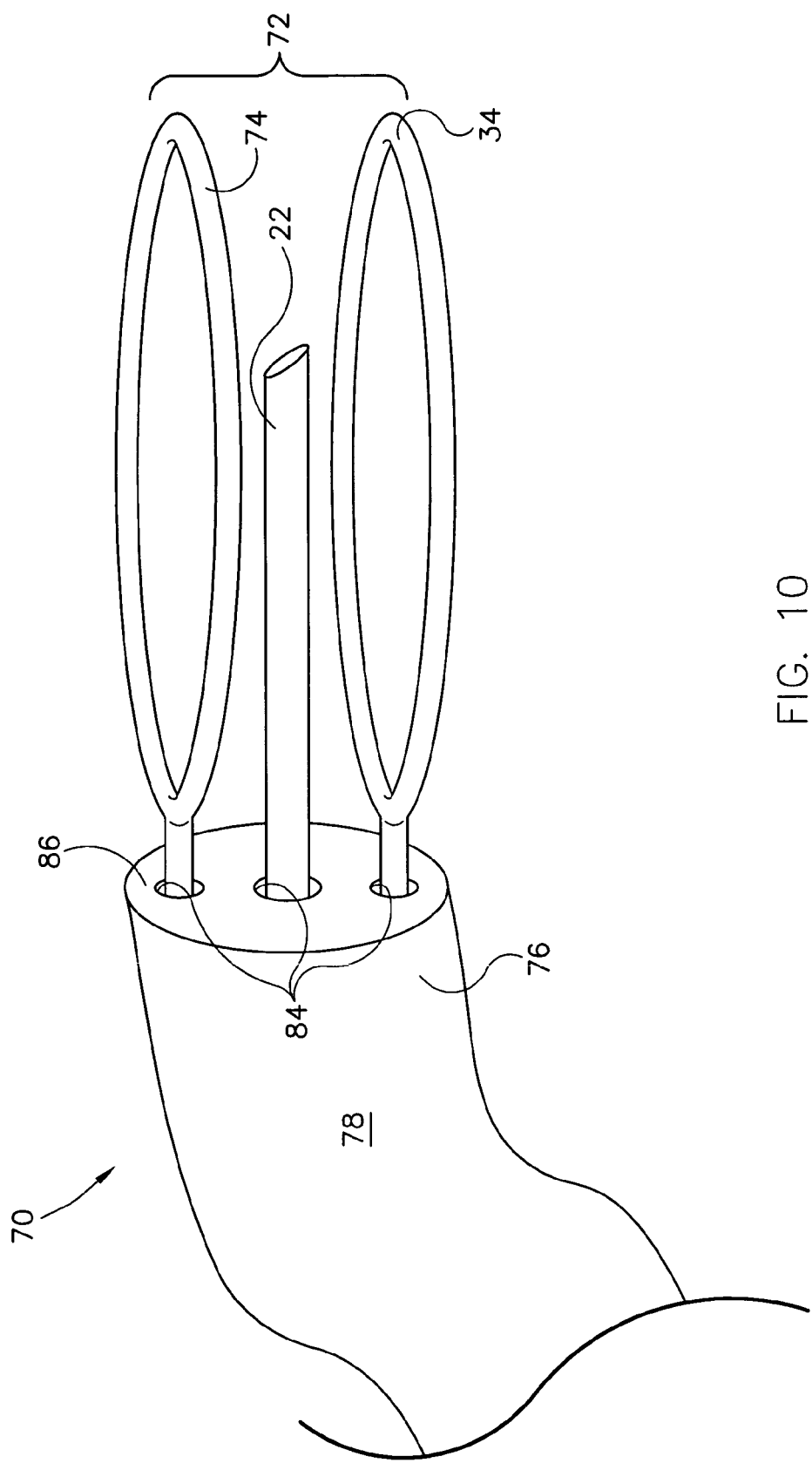
FIG. 10 is a perspective of the embodiment of FIG. 9 having the applicator elements slidably disposed within the probe.
Figure 11:
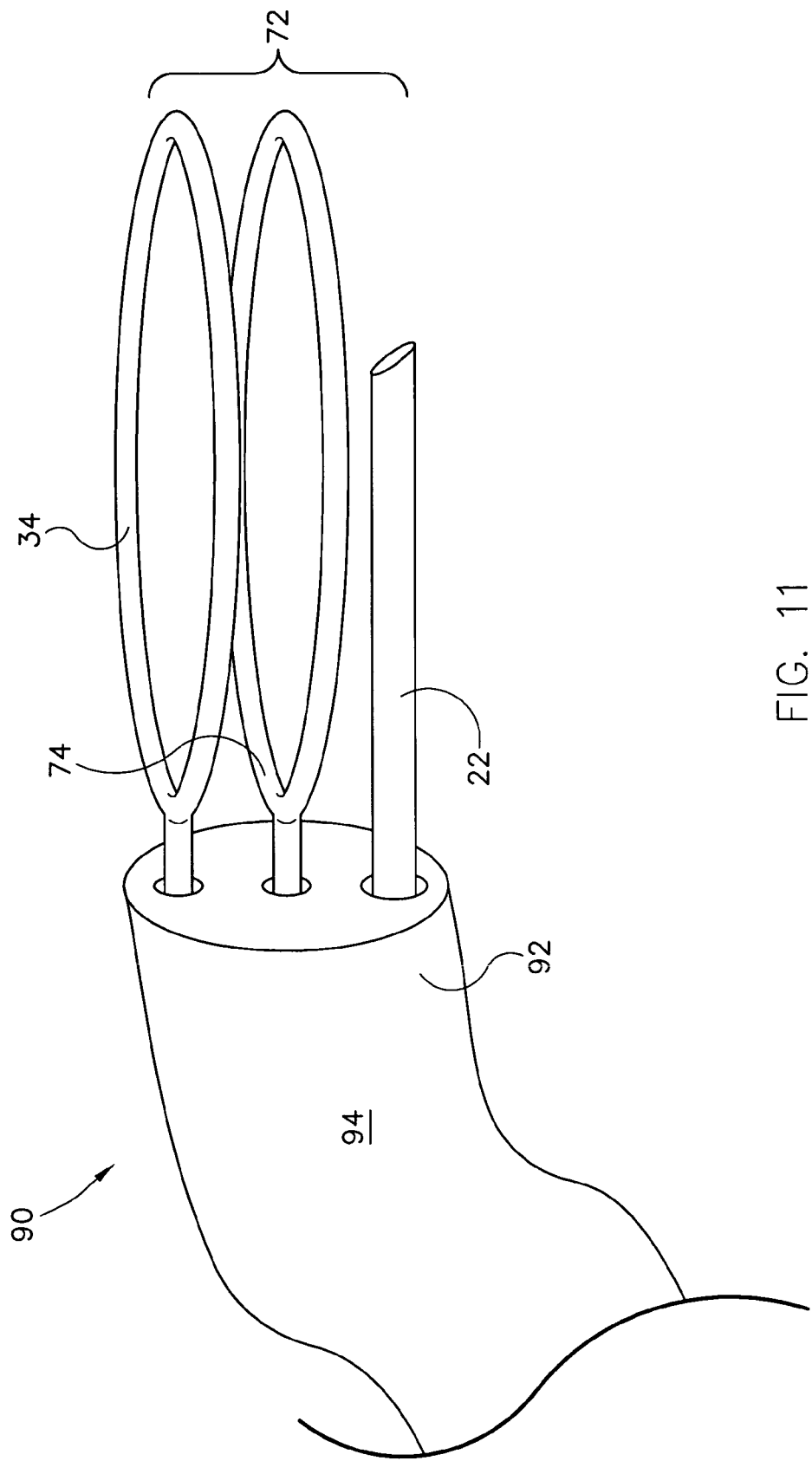
FIG. 11 is a perspective of a fourth embodiment of a medical device according to the present invention.

FIG. 9 shows a third embodiment of a medical device 70 according to the present invention wherein applicator elements 72 include a cutting loop 74 attached to an applicator end 76 of a probe 78. Although the cutting loop may have other dimensions without departing from the scope of the present invention, in one embodiment the cutting loop 74 has a diameter 80 of between about 0.5 millimeters and about 1.5 millimeters and an exposed length 82 of between about 10 millimeters and about 30 millimeters. Further, although the cutting loop may be made of other materials without departing from the scope of the present invention, in one embodiment the cutting loop 74 is made of stainless steel. The applicator elements 72 may be slidably disposed within respective channels 84 in the probe 78, as shown in FIG. 10. Thus, each of the applicator elements 72 can be moved between a deployed position, shown in FIG. 10, in which the elements 72 extend beyond a face 86 of the end 76 of the probe 78, and a stored position (not shown) in which the elements are fully disposed within the probe 78. Further, each of the elements 72 may be independently moved between their respective stored and deployed positions. Although FIG. 9 shows the needle 22 positioned between the ablating loop 34 and cutting loop 74, these elements may be arranged in other ways without departing from the scope of the present invention. For example, FIG. 11 shows a fourth embodiment of a medical device 90 according to the present invention having the cutting loop 74 positioned adjacent an applicator end 92 of a probe 94 between the needle 22 and the ablating loop 34. Also, although FIG. 9 shows each of the applicator elements 72 fixedly connected to the probe 78 and FIGS. 10 and 11 show each of the applicator elements slidably disposed within the probe, each of these elements 72 may relate to the probe 78, 94 in either manner. For example, in one embodiment of the present invention (not shown), the needle 22 is fixedly connected to the probe 78, 94 and the ablating and cutting loops 34, 74 are slidably disposed within the probe 78, 94. The probe 94, needle 22, and ablating loop 34 of the embodiments described in this paragraph are otherwise identical to those of the earlier described embodiments, and therefore will not be described in further detail.

Figure 12:
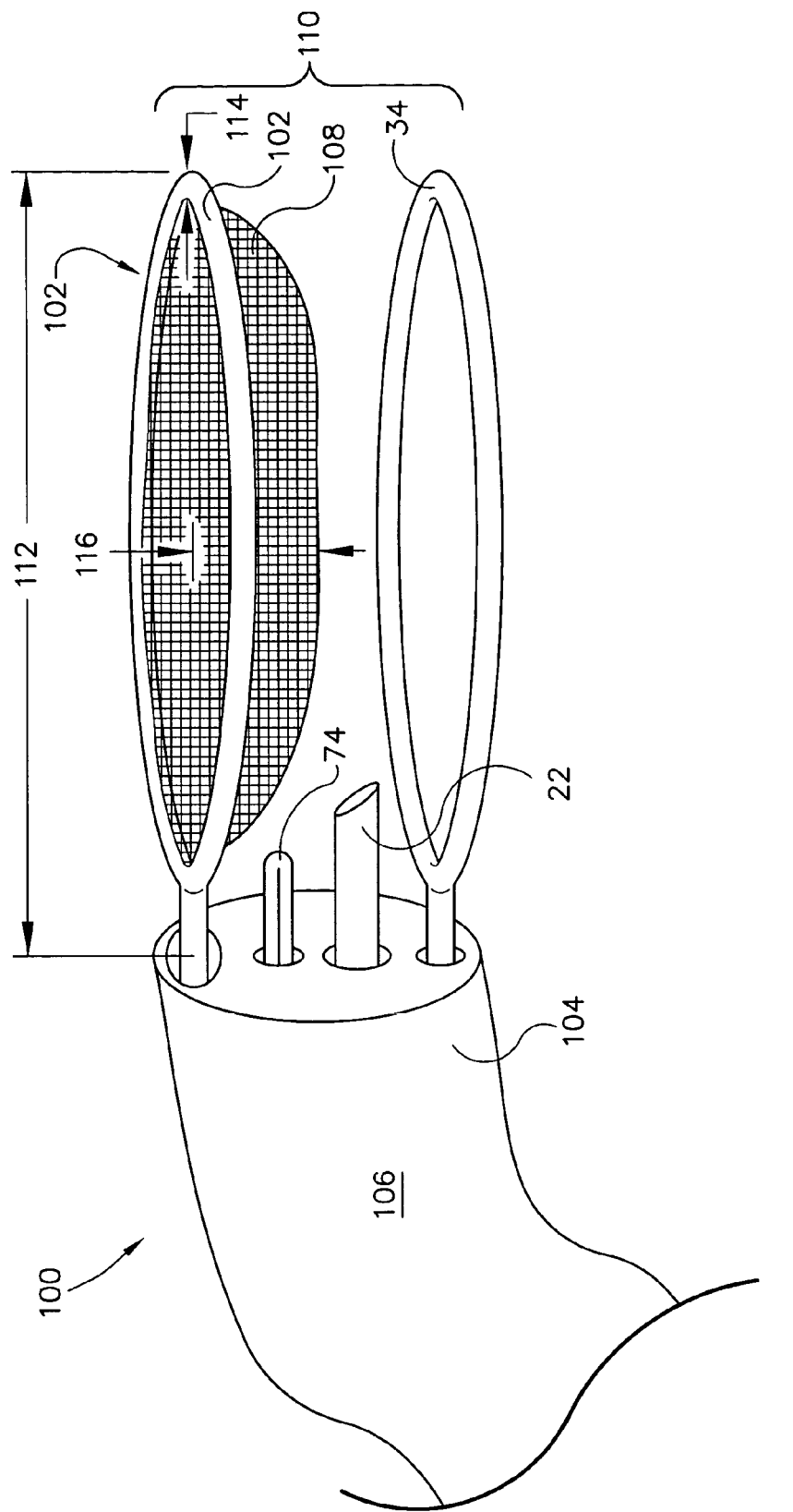
FIG. 12 is a perspective of a fifth embodiment of a medical device according to the present invention.

FIG. 12 shows a fifth embodiment of a medical device 100 according to the present invention having a retainer 102 attached to an applicator end 104 of a probe 106 to capture and hold tissue cut from the patient (not shown in FIGS. 1-14). Applicator elements 110 may be slidably disposed within the probe 106, as shown in FIG. 12. Thus, each of the applicator elements 110 can be moved between a deployed position, in which the applicator elements extend beyond the end 104 of the probe 106, and a stored position (shown in FIG. 21) in which the applicator elements are recessed within the probe 106. The needle 22 and cutting loop 74 are shown in FIG. 12 in an intermediate position between the stored and deployed positions and the ablating loop 34 and retainer 102 are shown in a deployed position. Further, each of the elements 110 may be independently moved between their respective stored and deployed positions. Although the retainer may be configured otherwise without departing from the scope of the present invention, in one embodiment the retainer 102 comprises netting 108 attached to the body of the retainer 102. Although the retainer may have other dimensions without departing from the scope of the present invention, in one embodiment the retainer 102 has an exposed length 112 of between about 10 millimeters and 30 millimeters and a body thickness 114 of between about 0.5 millimeters and about 1.5 millimeters. Further, although the net may have other depths without departing from the scope of the present invention, in one embodiment the net 108 has a depth 116 of between about 1 millimeter and about 5 millimeters. Instead of having a net 108, the retainer 102 may be configured to capture and hold the resected tissue in other ways without departing from the scope of the present invention. For example, in one embodiment (not shown) the retainer 102 may be connected to a suction source (not shown) to attract and retain the resected tissue by aspiration. The probe 106, needle 22, ablating loop 34, and cutting loop 74 of this embodiment are otherwise identical to those of the earlier described embodiments, and therefore will not be described in further detail.

Figure 13:
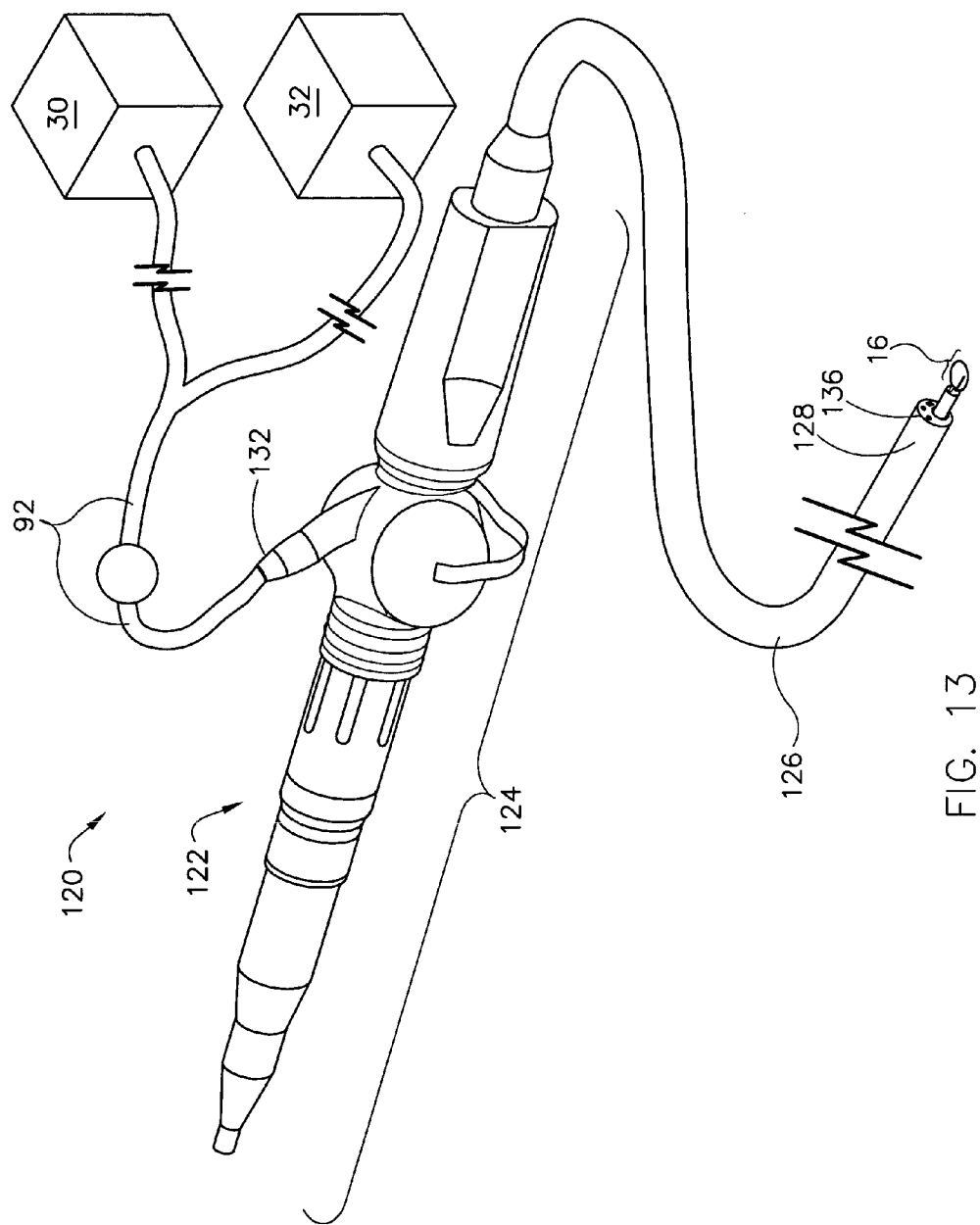
FIG. 13 is a perspective of the second embodiment of the device in combination with a conventional endoscope.

FIG. 13 shows an embodiment of a medical device 120 according to the present invention including an endoscope 122. Although FIG. 13 shows one type of endoscope 122, any conventional type of endoscope may be used without departing from the scope of the present invention. The endoscope 122 may be a flexible endoscope, such as those commonly used in upper gastrointestinal endoscopy examinations, or esophagogastroduodenoscopy (EGD). The endoscope 122 has an elongate primary body 124 and an elongate tubular portion 126 (e.g., a flexible shaft) extending from the body 124 to a working end 128. The endoscope 122 also has a working channel 130 beginning at an entry orifice 132 on the primary body 124 and terminating at a terminal port 134 at an extreme end 136 of the shaft 126. The working channel of conventional endoscopes has a diameter, or minimum width if non-circular, of about three millimeters. In one embodiment of the present invention, the probe 56, needle 22, and ablating loop 34 are sized and shaped for slidable receipt within the working channel 130 of the endoscope 122. The probe 56, needle 22, and ablating loop 34 of this embodiment are otherwise identical to those of the earlier described embodiments, and therefore will not be described in further detail.

Figure 14:
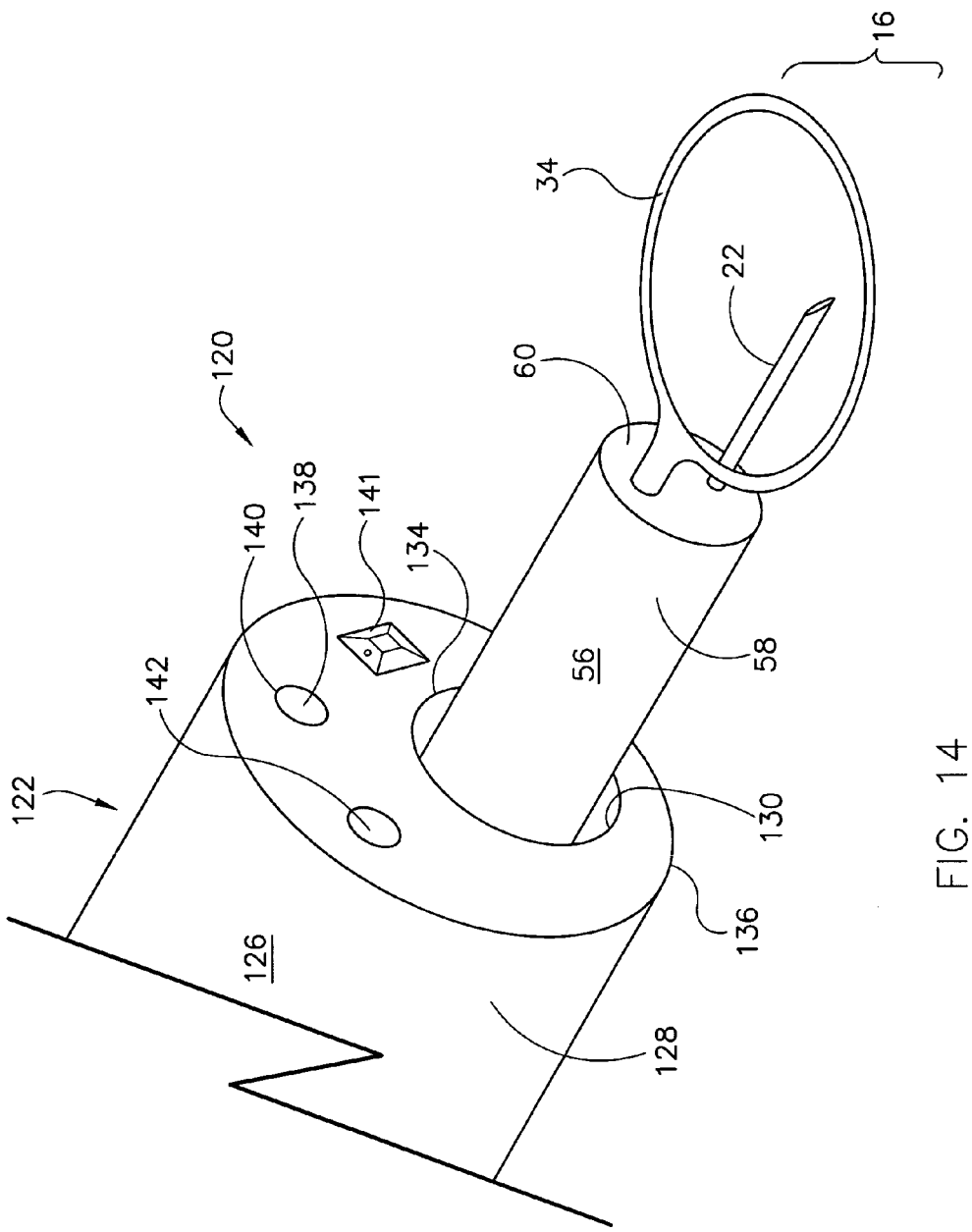
FIG. 14 is a perspective of a portion of the combination shown in FIG. 13.

As shown in FIG. 14, the medical device 120 can have viewing optics 138 for viewing an object (not shown) positioned in a viewing area (not shown) adjacent the working end 128 of the endoscope 122. The viewing area comprises all the objects visible through the viewing optics 138, including the applicator elements 16 and adjacent patient tissue (not shown in FIGS. 1-14). Although the viewing area may have other shapes without departing from the scope of the present invention, in one embodiment the area is circular. The optics 138 are disposed within the endoscope 122, beginning at a location (not shown) adjacent the primary body 124, where a user may receive images, and terminating adjacent an optics orifice 140. The endoscope 122 can also have a cleaning tab 141 for cleaning the optics 138 by forcing fluid against a lens (not shown) covering an end of the optics adjacent the working end 128 of the endoscope. Although the cleaning tab 141 may be made of other materials without departing from the scope of the present invention, in one embodiment the cleaning tab is made of metal. The cleaning tab 141 can be connected to the same fluid source 32 connected to the needle 22 or a separate fluid source (not shown) for delivering fluid to the cleaning tab during operation of the device 120. Although the cleaning tab 141 may force other fluids against the lens of the optics 138 without departing from the scope of the present invention, in one embodiment the cleaning tab forces water against the lens. The endoscope 122 also has an illuminator 142 for directing light toward an object (not shown) positioned adjacent the working end 128 of the shaft 126. As with the optics 138, the illuminator 142 originates at a location (not shown) adjacent the primary body 124 and terminates adjacent the extreme end 136 of the shaft 126.

A primary purpose for the medical device is to ablate and/or remove unwanted abnormal tissue growths. Although the medical device is described as ablating and removing abnormal gastrointestinal polyps and lesions in humans, the device may ablate other tissues, tissues in other animals, or things other than tissue without departing from the scope of the present invention.

Figure 15:
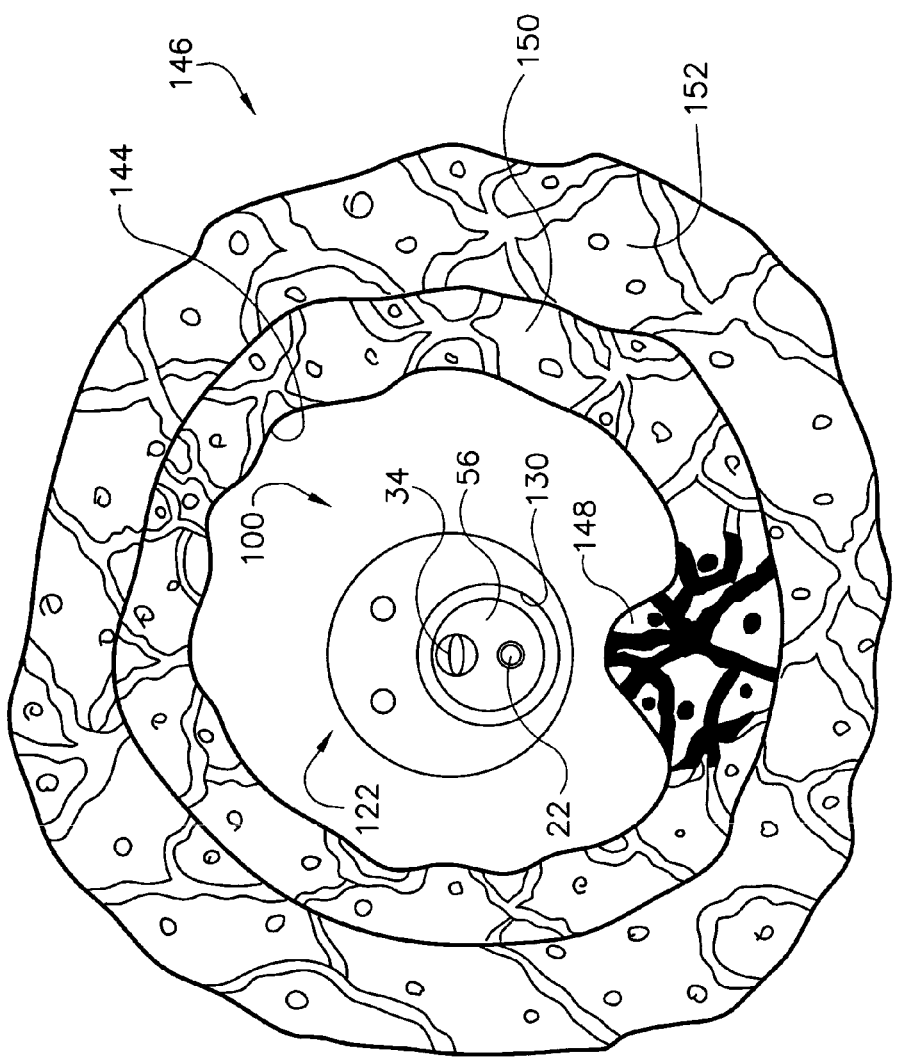
FIG. 15 is a cross-sectional front elevation of the combination shown in FIG. 14 positioned in a patient with applicator elements stored in the probe.

In operation, a user of the medical device 120 first positions the elongate probe 56 in the working channel 130 of the endoscope 122. The injection needle 22 and ablating loop 34 are connected to an energy source 30 and the injection needle 22 is further connected to a fluid source 32. The probe 56, needle 22, ablating loop 34, and energy source 30 can be the same as any of the earlier described embodiments, and therefore will not be described in further detail. FIG. 15 shows the probe 56 slidably disposed in the working channel 130 of the endoscope 122 and the endoscope/probe combination disposed within a cavity or lumen 144 such as an esophagus of a patient 146. The user moves the endoscope 122 and probe 56 to a predetermined location within the patient 146. If desired, the user can verify that the probe 56 and endoscope 122 are properly positioned by viewing the patient 146 and applicator elements 16 positioned at the end 58 of the probe 56. The predetermined location is adjacent abnormal tissue growth 148, such as a lesion or polyp. Positioning the endoscope 122 and probe 56 may include articulating the shaft 126 of the endoscope 122, translating the endoscope 122, rotating the probe 56 with respect to the endoscope 122, and/or translating the probe 56 with respect to the endoscope 122.

Figure 16:
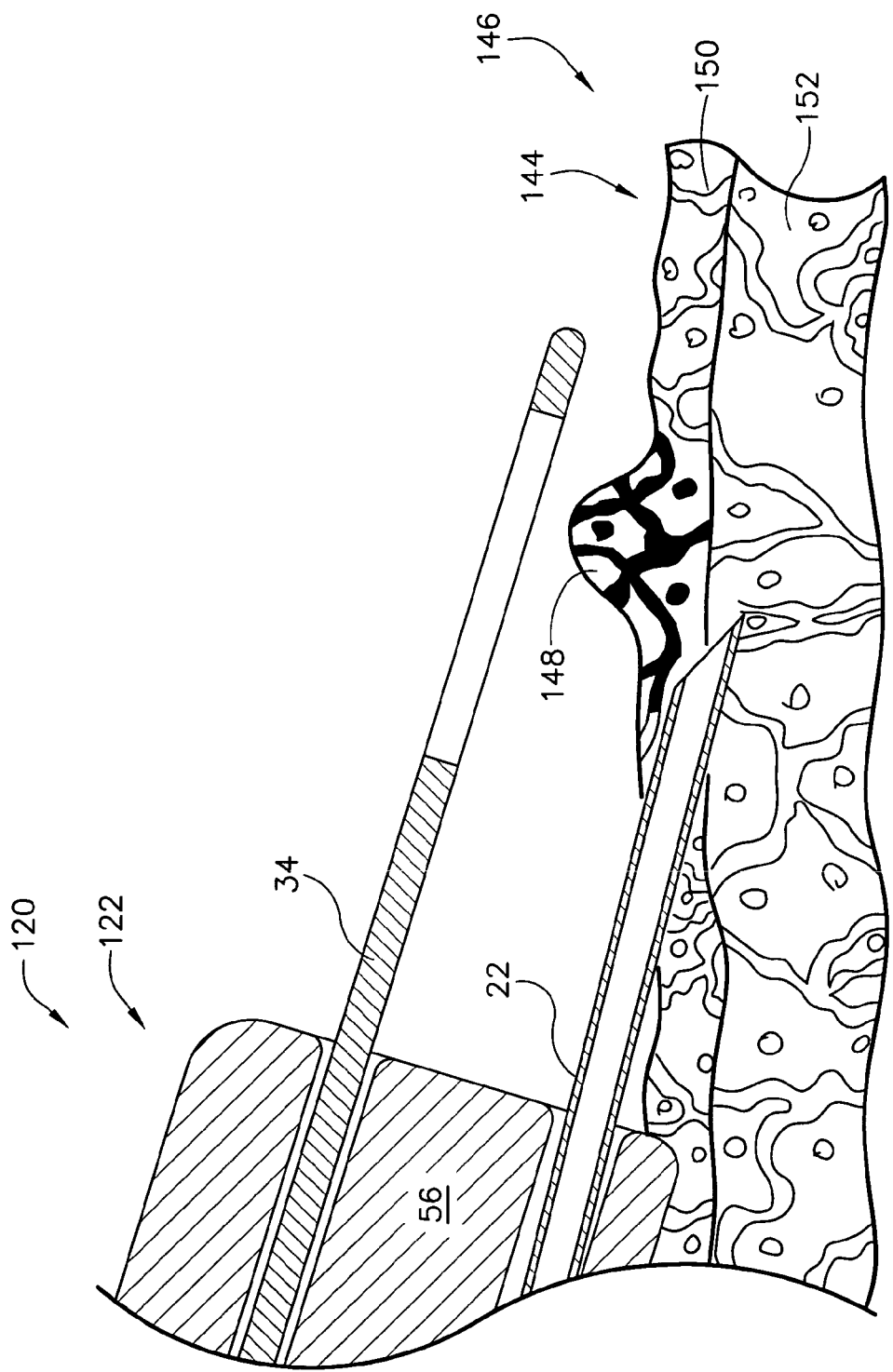
FIG. 16 is a cross-sectional side elevation of FIG. 15 shown after the needle has been inserted into the tissue.
Figure 17:
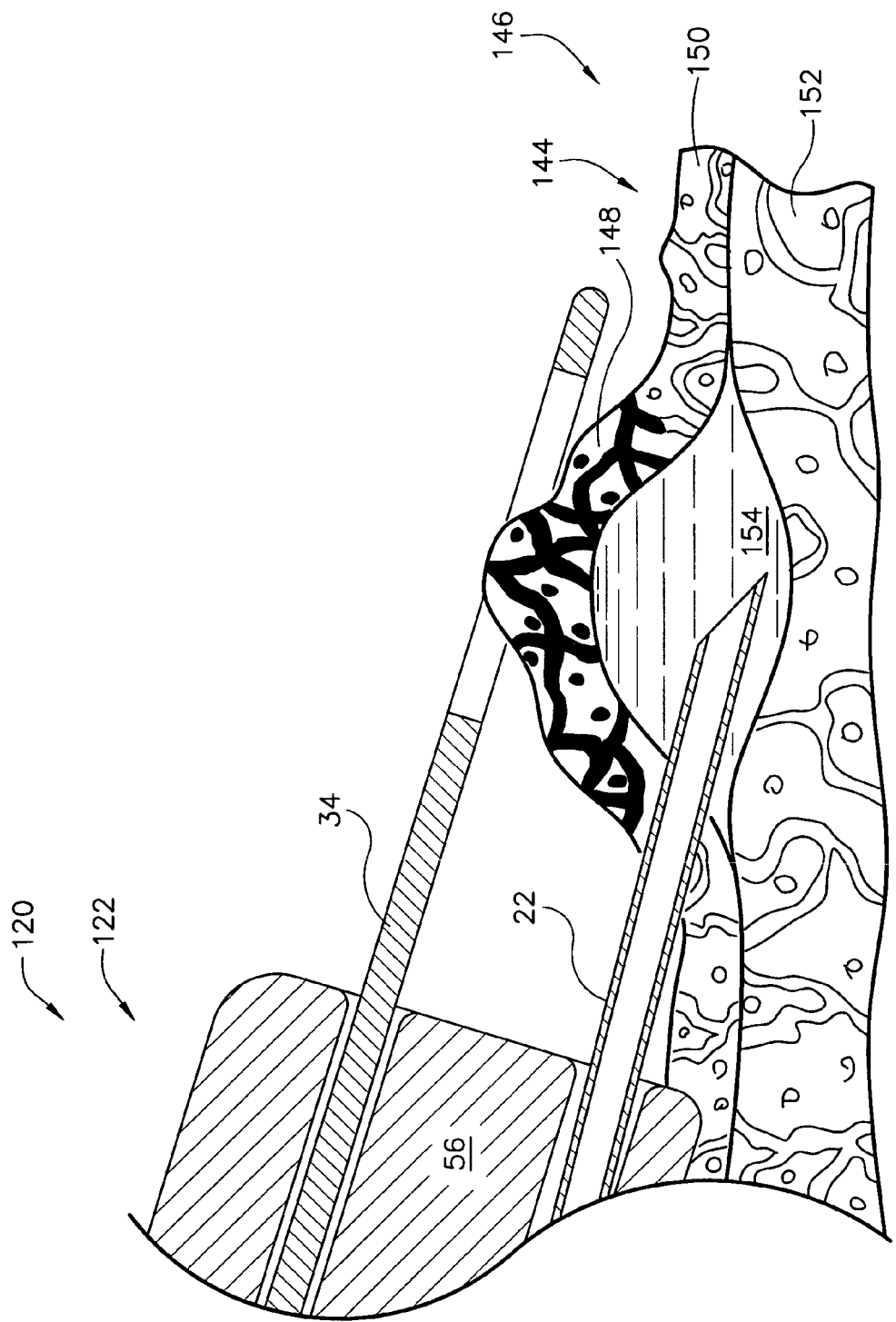
FIG. 17 is the cross-sectional side elevation of FIG. 16 shown after fluid has been injected through the needle into the tissue.
Figure 18:
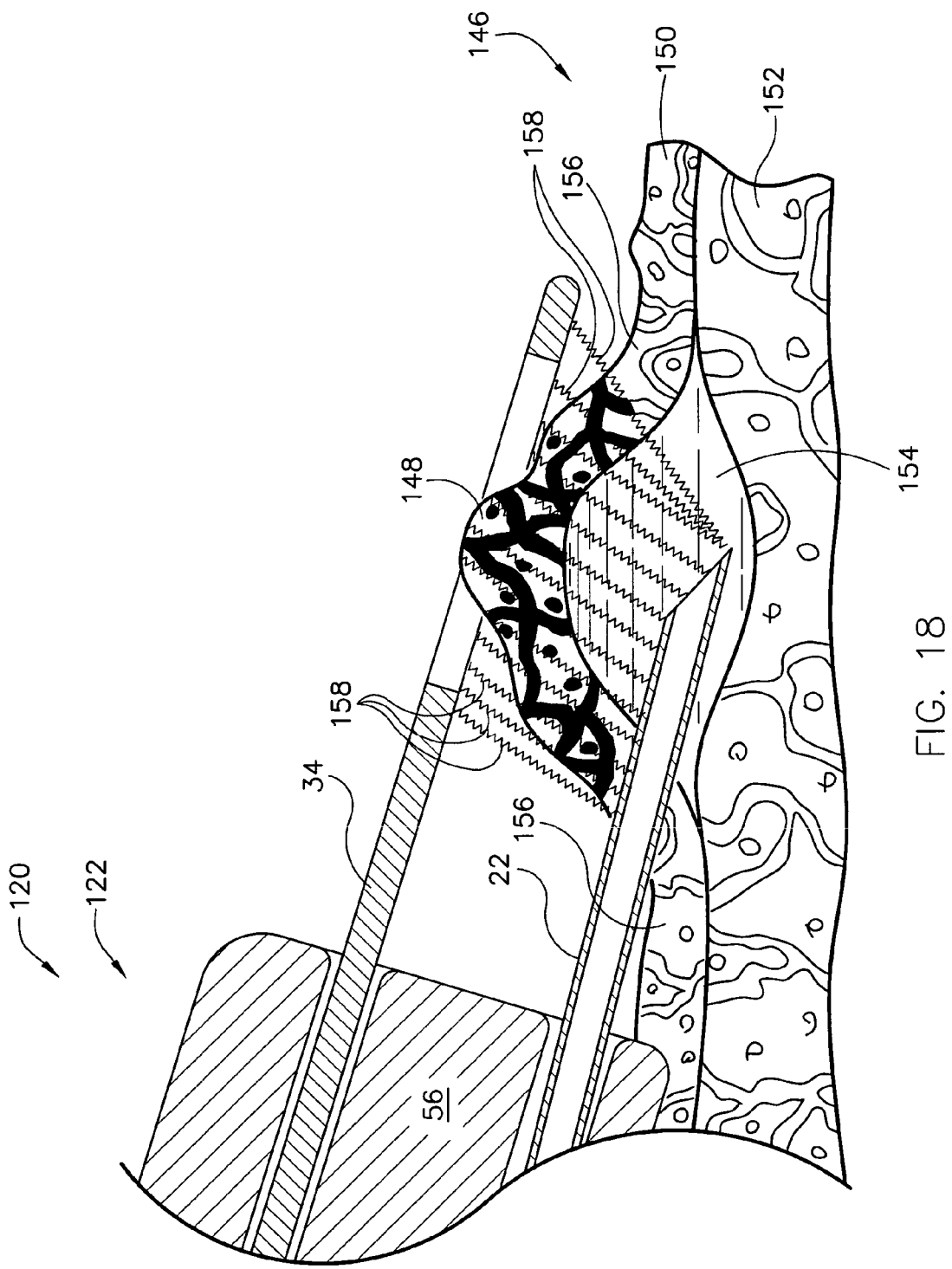
FIG. 18 is the cross-sectional side elevation of FIG. 17 shown during ablation of target tissue.

Once the medical device 120 has been positioned as described, the user deploys the needle 22 such that the needle extends through the port 134 of the working channel 130 at the working end 128 of the endoscope 122. The user also deploys the ablating loop 34 such that the loop 34 extends through the port 134 of the endoscope 122. The user may deploy the ablating loop 34 at the same time as, before, or after the needle 22 is deployed. Then, the user causes the needle 22 to contact the patient 146 adjacent the abnormal growth 148 and advance below an inner or mucosal layer 150 of the lumen 144. In one embodiment, it is preferred that the needle 22 is forced to a position between the inner layer 150 and a muscular layer 152 underlying the inner layer 150, as shown in FIG. 16. After the needle 22 is forced below the inner layer 150, fluid 154 is injected into the lumen 144 through the needle 22, thereby causing the inner layer 150 adjacent the abnormal growth 148 to move away from the muscular layer 152, as shown in FIG. 17. Then, the user can destroy the targeted tissue 148 of the patient 146 located between the needle 22 and ablating loop 34 by simultaneously energizing the needle and ablating loop thereby causing energy 158 to transfer through the target tissue, as shown in FIG. 18. During the ablation of the growth 148, the injection needle 22 and the ablating loop 34 can carry opposite polarities. Further, the polarities of the needle 22 and ablating loop 34 can change with time.

Figure 19:
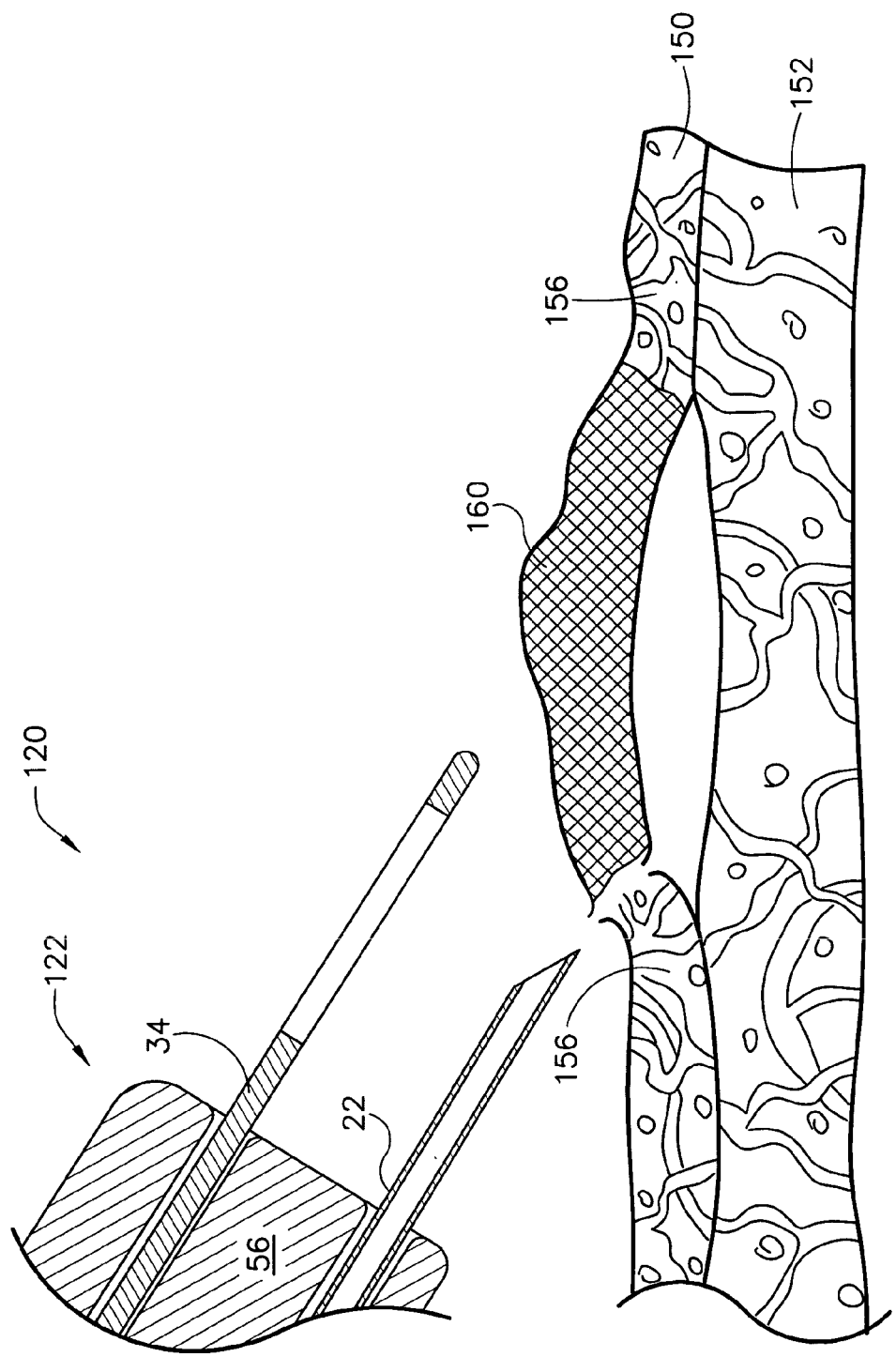
FIG. 19 is the cross-sectional side elevation of FIG. 18 shown after ablation of the target tissue and removal of the needle from the patient tissue.

During the ablation, healthy adjacent tissue 156 of the inner layer 150 is substantially unharmed because the energy transmission focuses between the needle 22 and ablating loop 34, where the diseased tissue 148 is located but the healthy adjacent tissue is not. The healthy underlying tissue 152 is also substantially unharmed during ablation because the injection of fluid into the lumen 144 causes the muscular tissue 152 to be spaced from the target tissue 148 and the energy transmission focuses between the needle 22 and the ablating loop 34. After ablation, the user can remove the needle 22 from the patient 146, as shown in FIG. 19. A short period of time after the procedure, the destroyed tissue 160 will be sloughed off (i.e., through the normal digestive process) and healthy mucosal tissue 150 will grow in its place. In embodiments of the device also having a cutting loop 74, the destroyed tissue 160 may be resected after ablation. In embodiments of the device having a cutting loop 74 and a retainer 102, the destroyed tissue may be captured and held in the retainer 102 after being cut from the patient with the cutting loop 74.

By this local and accurate ablation method, diseased mucosal tissue 148 is destroyed and healthy underlying muscular tissue 152 and adjacent mucosal tissue 156 of the inner layer 150 are substantially unharmed. The type of energizing may be of any conventional type, including the types mentioned above regarding energy source 30, such as radio frequency, electrical, and ultrasonic. Although this embodiment of a therapeutic method according to the present invention was described with reference to medical device 122, it will be appreciated by those skilled in the art that the method can be performed in a substantially similar manner using other disclosed embodiments without departing from the scope of the present invention.

Figure 20:
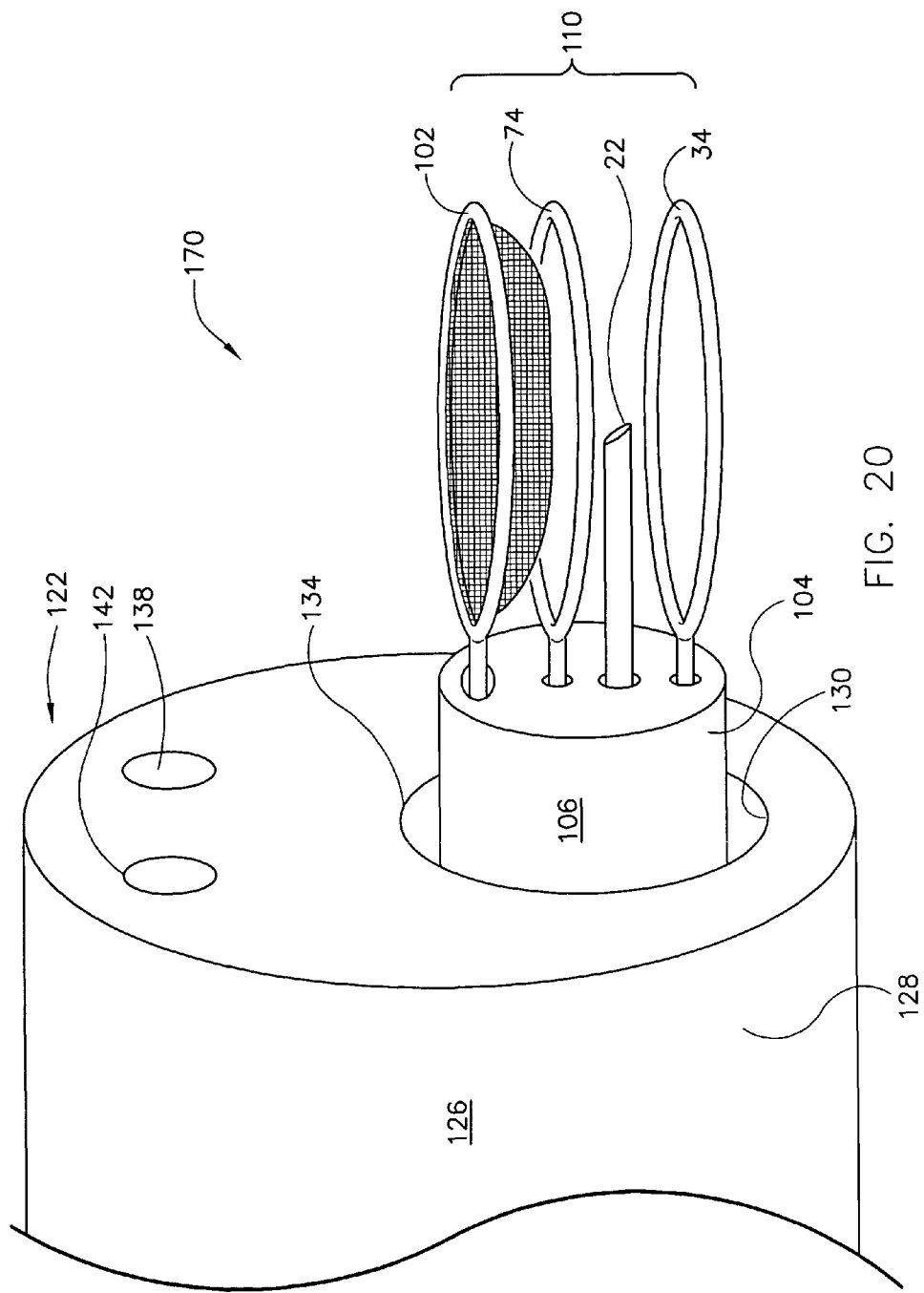
FIG. 20 is a perspective of the fifth embodiment of the present invention in combination with a conventional endoscope.
Figure 21:
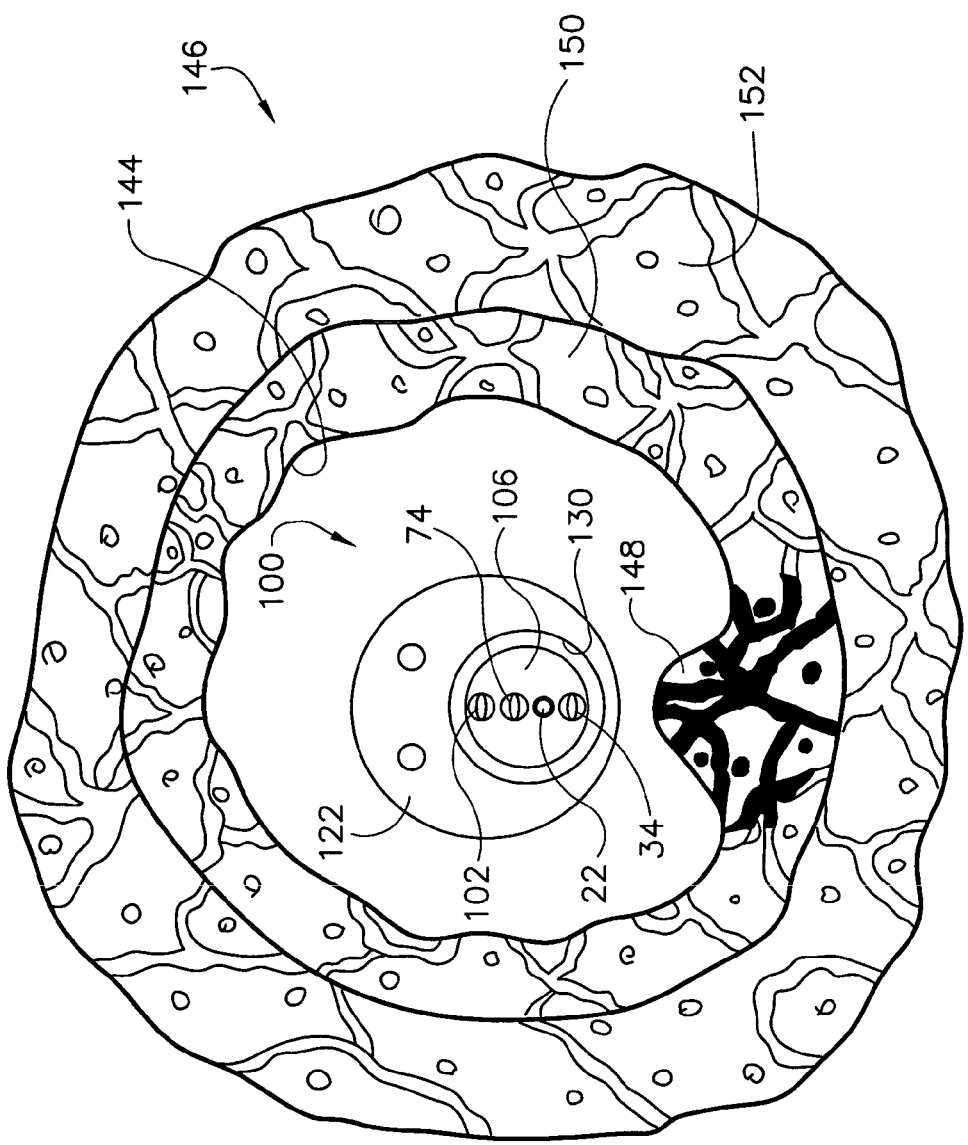
FIG. 21 is a cross-sectional front elevation of FIG. 20 positioned in a patient with applicator elements stored in the probe.

FIG. 20 shows an embodiment of a medical device 170 according to the present invention including an endoscope 122. In use, a user positions an elongate probe 106 having a needle 22, ablating loop 34, cutting loop 74, and retainer 102 in the working channel 130 of the endoscope 122. The injection needle 22 and ablating loop 34 are connected to an energy source 30 and the injection needle 22 is further connected to a fluid source 32. The endoscope 122, probe 106, needle 22, cutting loop 74, retainer 102, ablating loop 34, and energy source 30 can be the same as any of the earlier described embodiments, and therefore will not be described in further detail. FIG. 21 shows the probe 106 slidably disposed in the working channel 130 of the endoscope 122 and the endoscope/probe combination disposed within a lumen 144 of a patient 146. The user then moves the endoscope 122 and probe 106 to a predetermined location adjacent abnormal tissue growth 148 as described regarding earlier embodiments.

Figure 22:
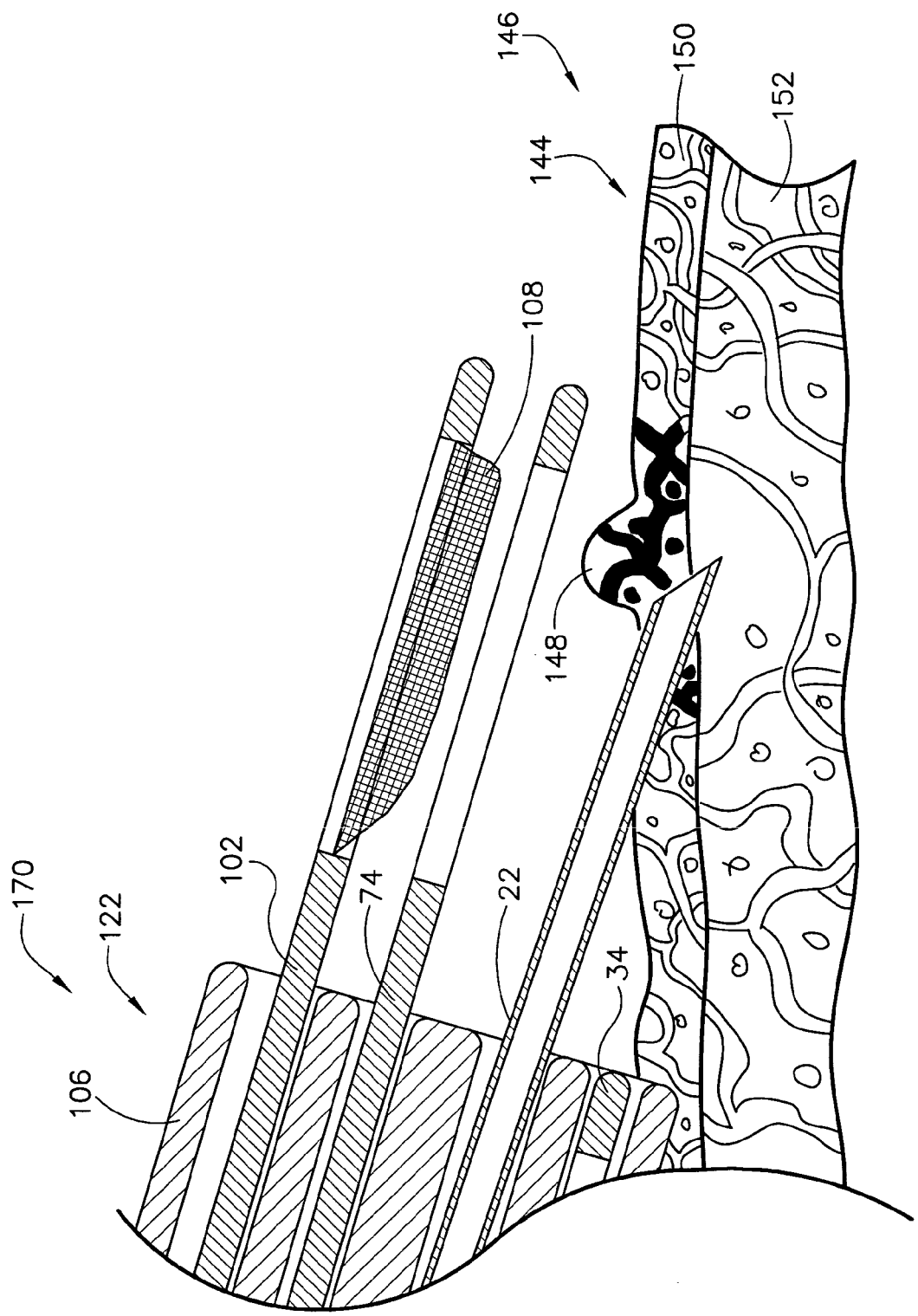
FIG. 22 is a cross-sectional side elevation of the combination shown in FIG. 21 shown after the retainer, cutting loop, and needle have been deployed and the needle has been inserted into the tissue of the patient.
Figure 23:
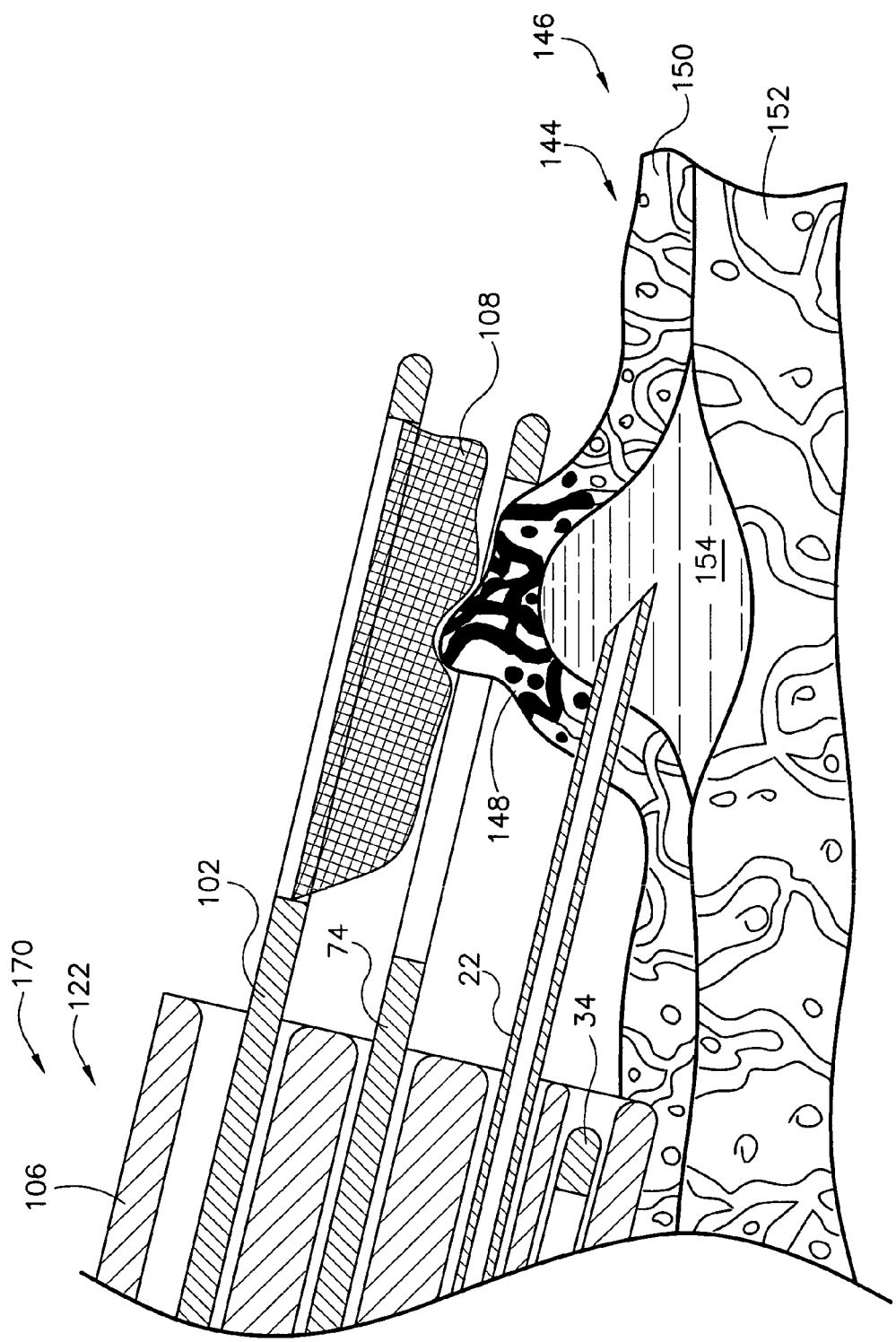
FIG. 23 is the cross section of FIG. 22 shown after fluid has been injected through the needle into the tissue.
Figure 24:
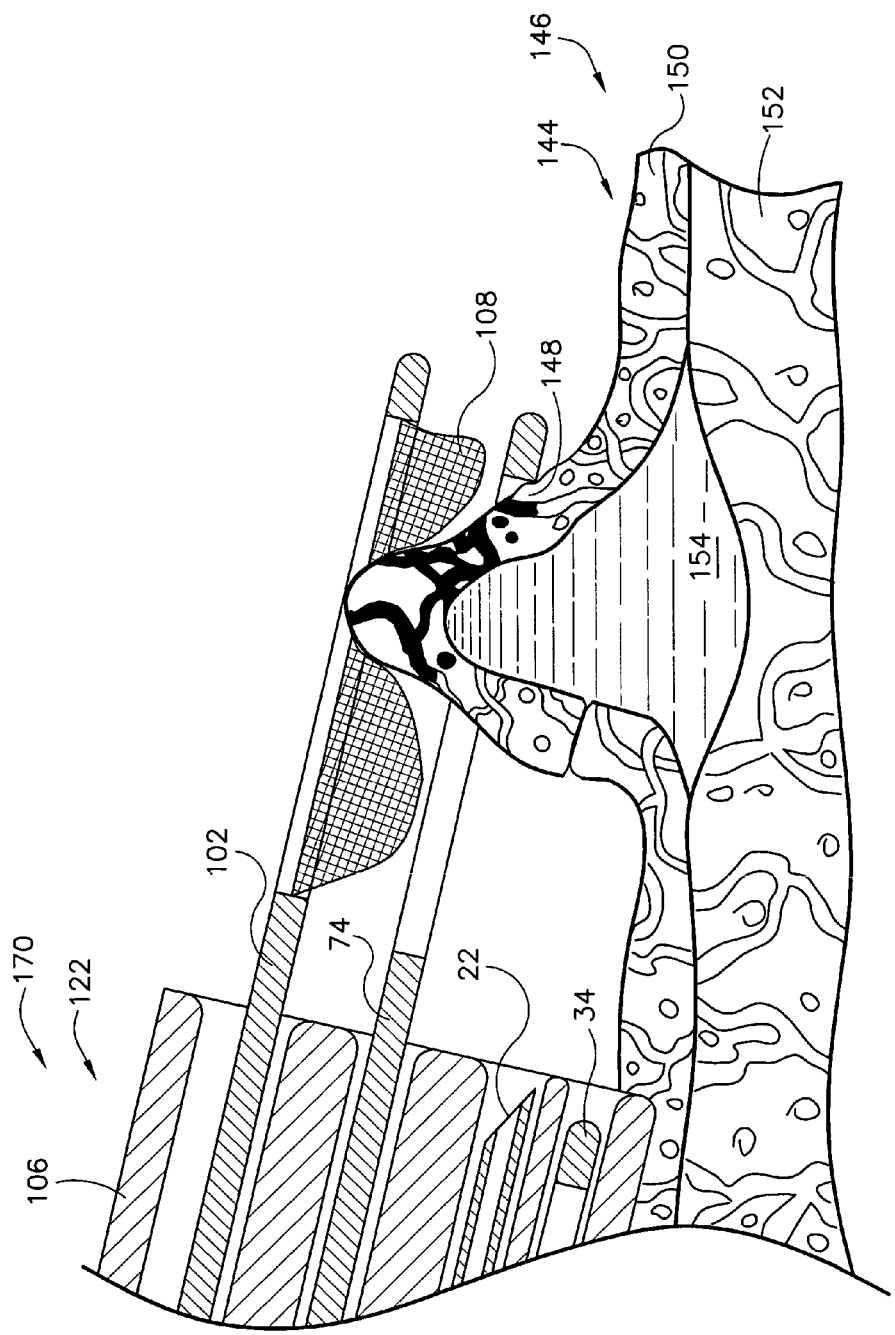
FIG. 24 is the cross section of FIG. 23 shown after the needle has been retracted into the probe and the cutting loop and retainer have been positioned for cutting away and capturing the target tissue.
Figure 25:
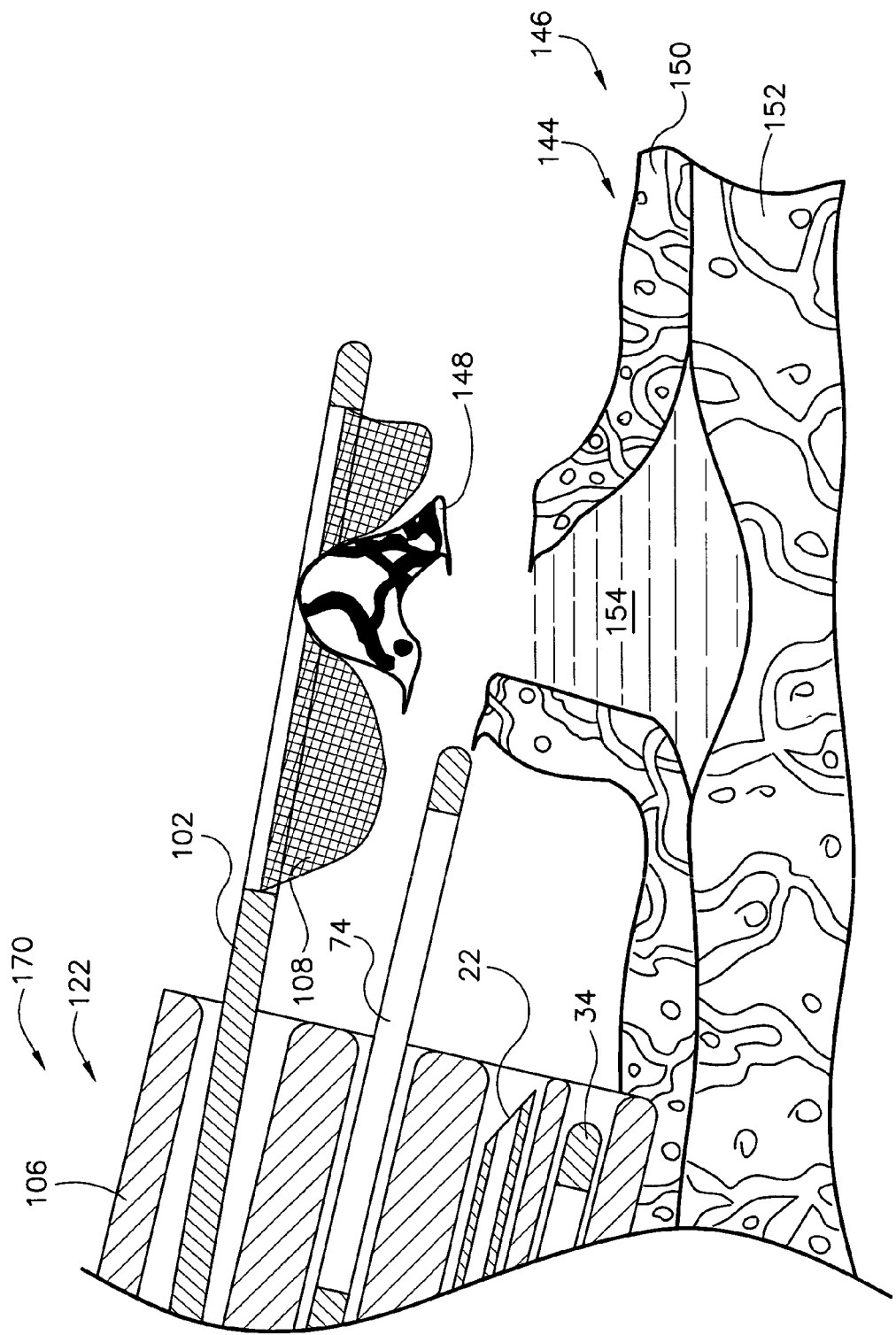
FIG. 25 is the cross section of FIG. 24 shown after the target tissue has been cut from the patient with the cutting loop.
Figure 26:
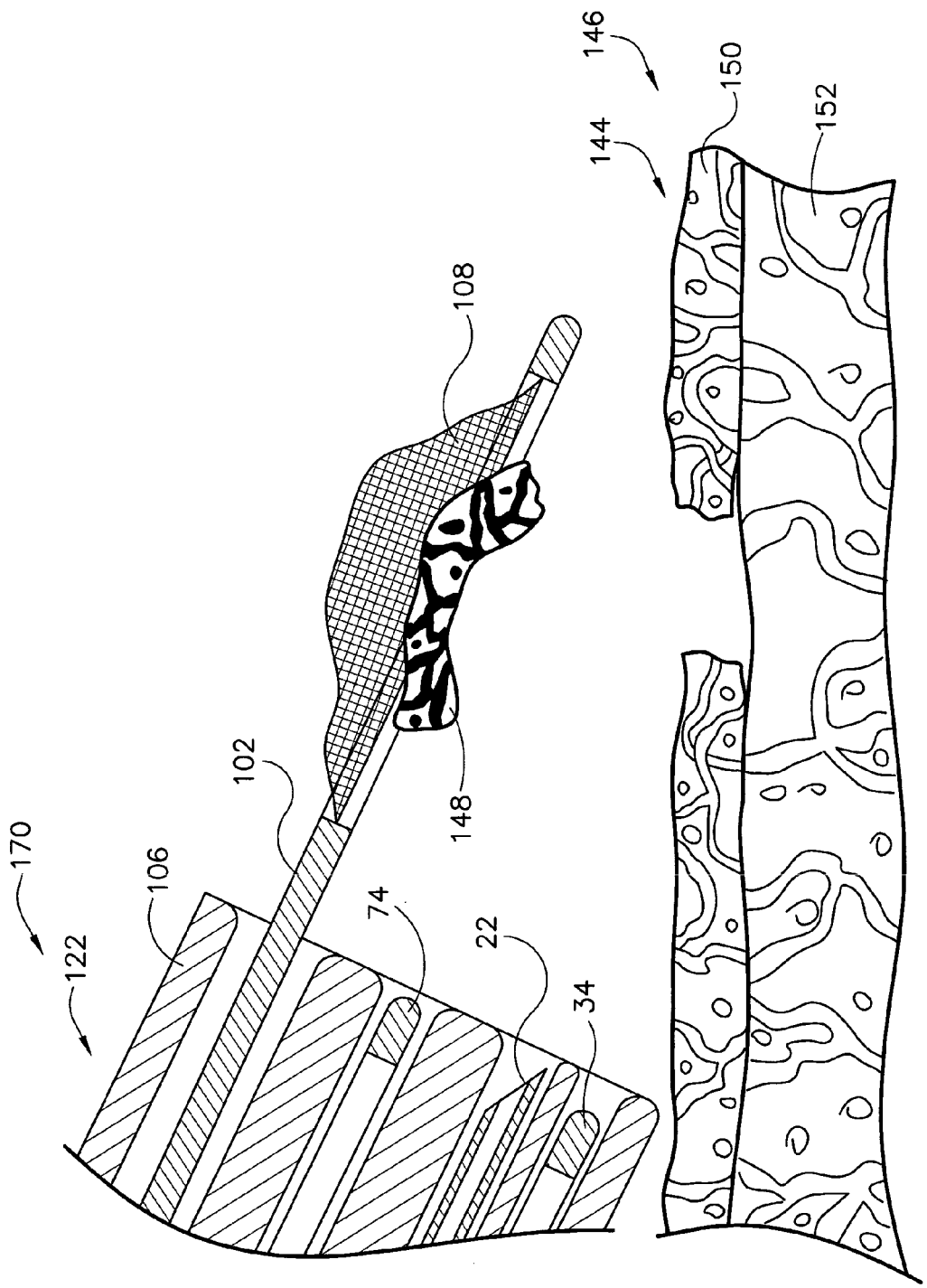
FIG. 26 is the cross section of FIG. 25 shown during capture of the target tissue in the retainer.
Figure 27:
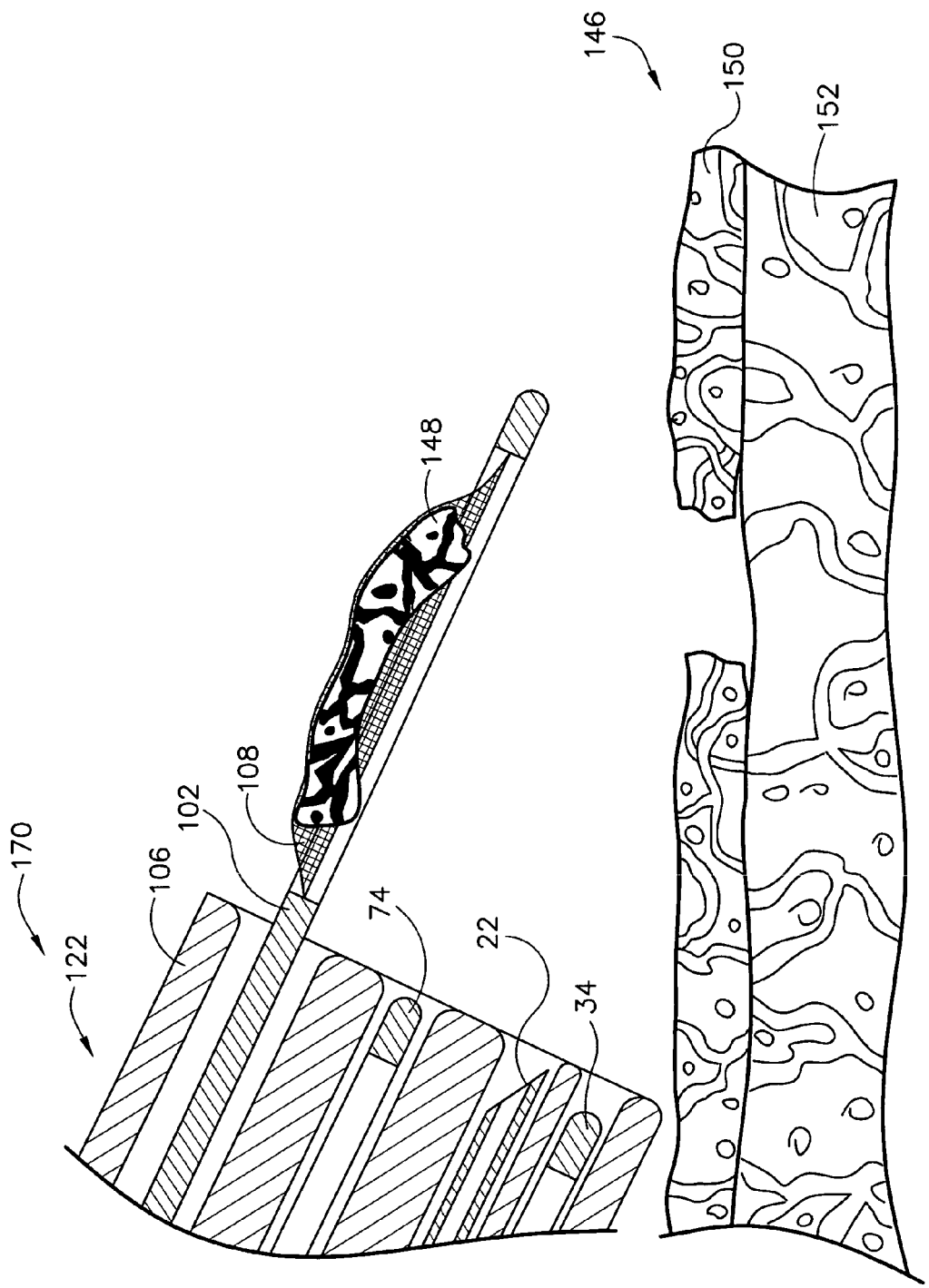
FIG. 27 is the cross section of FIG. 26 shown after the target tissue has been captured in the retainer.
Figure 28:
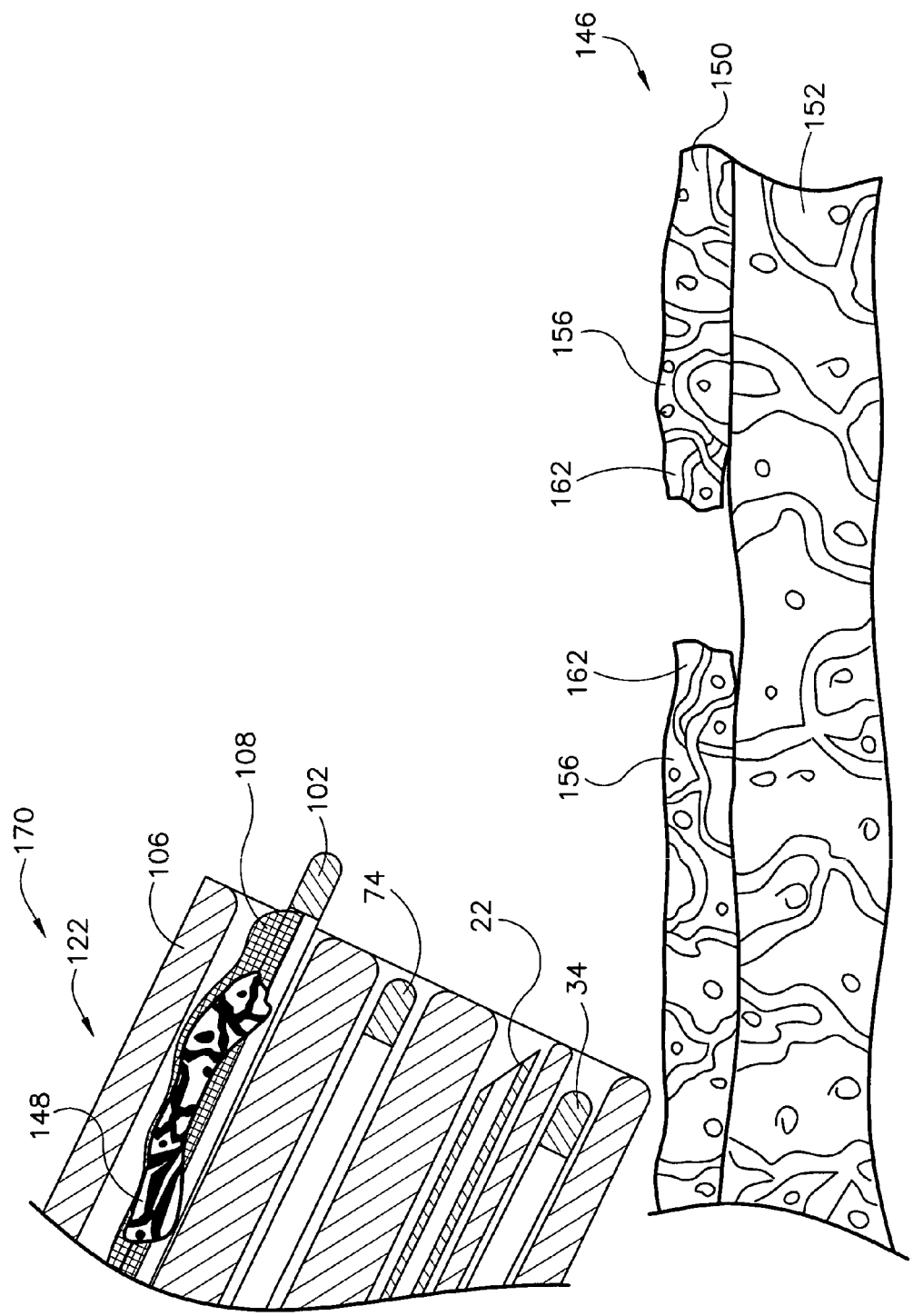
FIG. 28 is the cross section of FIG. 27 shown after the retainer has been retracted into the probe with the captured tissue.

Once the medical device 170 has been positioned as described, the user deploys the needle 22 such that the needle extends through the port 134 of the working channel 130 at the working end 128 of the endoscope 122. The user also deploys the cutting loop 74 such that the cutting loop 74 extends through the port 134 of the endoscope 122. Further, the user deploys the retainer 122 such that the retainer 122 also extends through the port 134 of the endoscope 122. The user may deploy the applicator elements 110 in any order and may deploy some or all of the elements 110 simultaneously. For example, the needle 22, cutting loop 74, and retainer 122 can be deployed simultaneously before the ablating loop 34 is deployed. Next, the user causes the needle 22 to contact the patient 146 adjacent the abnormal growth 148 and advance below the inner layer 150 of the lumen 144. In one embodiment, it is preferred that the needle 22 is forced to a position between the inner layer 150 and the muscular layer 152 underlying the inner layer 150, as shown in FIG. 22. After the needle 22 is forced below the inner layer 150, fluid 154 is injected into the lumen 144 through the needle 22, thereby causing the inner layer 150 adjacent the abnormal growth 148 to move away from the muscular layer 152, as shown in FIG. 23. Spacing the abnormal growth above the muscular layer 152 by injecting fluid 154 facilitates accurate cutting away of the abnormal tissue 148 without adversely affecting adjacent and underlying healthy tissue 156, 152. Also, isolating the unwanted tissue 148 from the healthy tissue 156, 152 allows the user to resect a larger amount of tissue than can be safely resected without such isolation. After injecting fluid 154 into the lumen 144, the user can remove the needle from the tissue of the lumen 144, position the cutting loop 74 to cut the abnormal growth 148 from the patient, and position the retainer 102 to capture and hold the growth 148 after it is cut. FIG. 24 shows an example of such positioning of the cutting loop 74 and retainer 102. Positioning the cutting loop 74 for cutting the growth 148 includes surrounding the growth 14 with the cutting loop 74. Positioning the retainer 102 for capturing the growth 148 includes positioning the retainer 102 such that the growth 128 will naturally fall into the net 108 of the retainer after it is cut from the patient 146 or such that the retainer 102 can be maneuvered to capture the growth 148 after it is cut from the patient 146. After the cutting loop 74 and retainer 102 are positioned for cutting and capturing as described, the cutting loop 74 is withdrawn into the probe 106 thereby cutting the abnormal growth 148 from the patient 146, as shown in FIG. 25. After cutting, if the growth 148 did not fall into the net 108 of the retainer 102, the retainer can be maneuvered to capture the growth 148, as exemplified in FIGS. 26 and 27. Once the growth 148 is caught in the net 108 of the retainer 102 as described, the retainer is withdrawn into the probe 106, as shown in FIGS. 27 and 28. In this way, the abnormal growth 148 can be removed from the patient for analysis.

Figure 29:
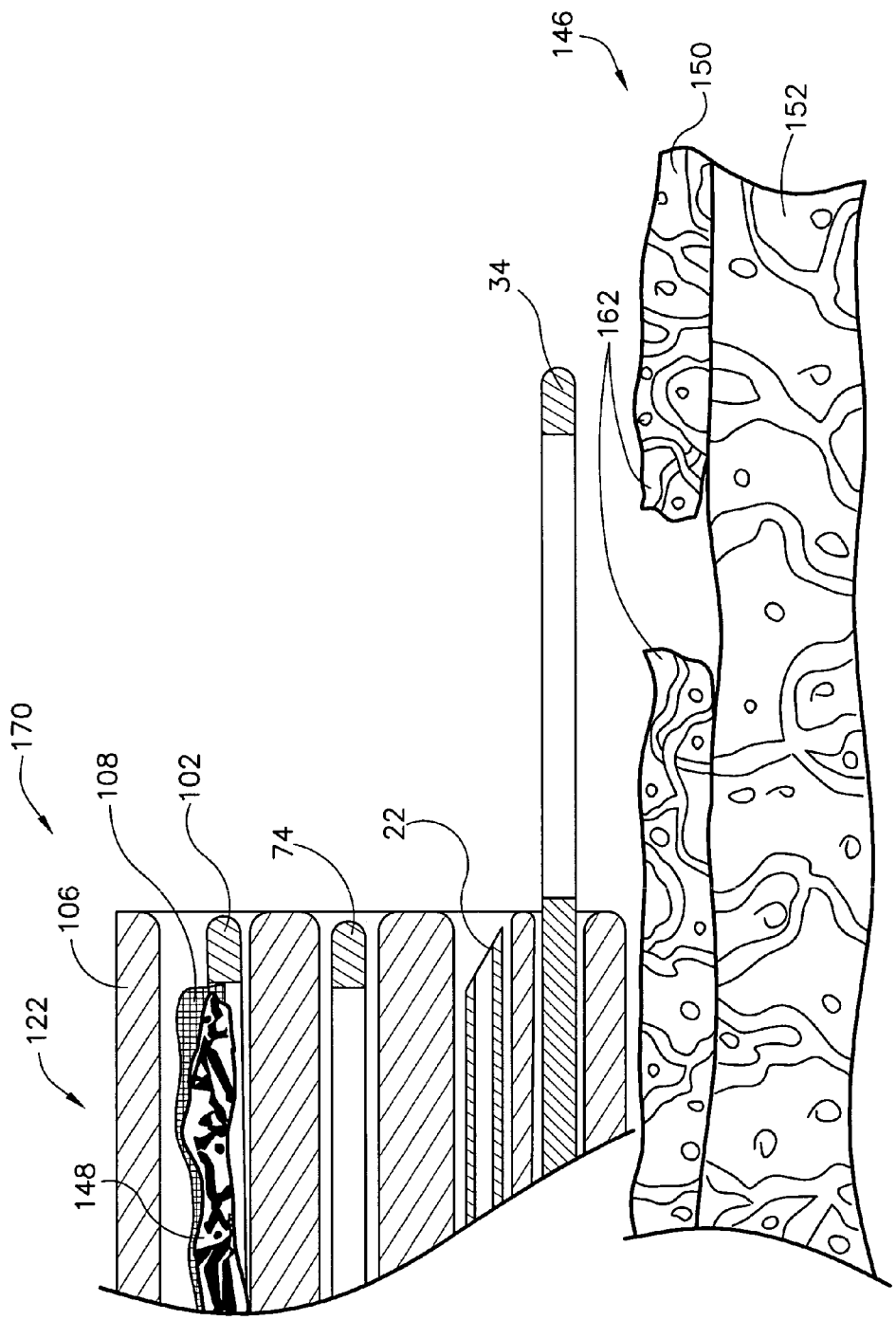
FIG. 29 is the cross section of FIG. 28 shown after the ablating loop has been positioned adjacent edges of tissue remaining in the patient.
Figure 30:
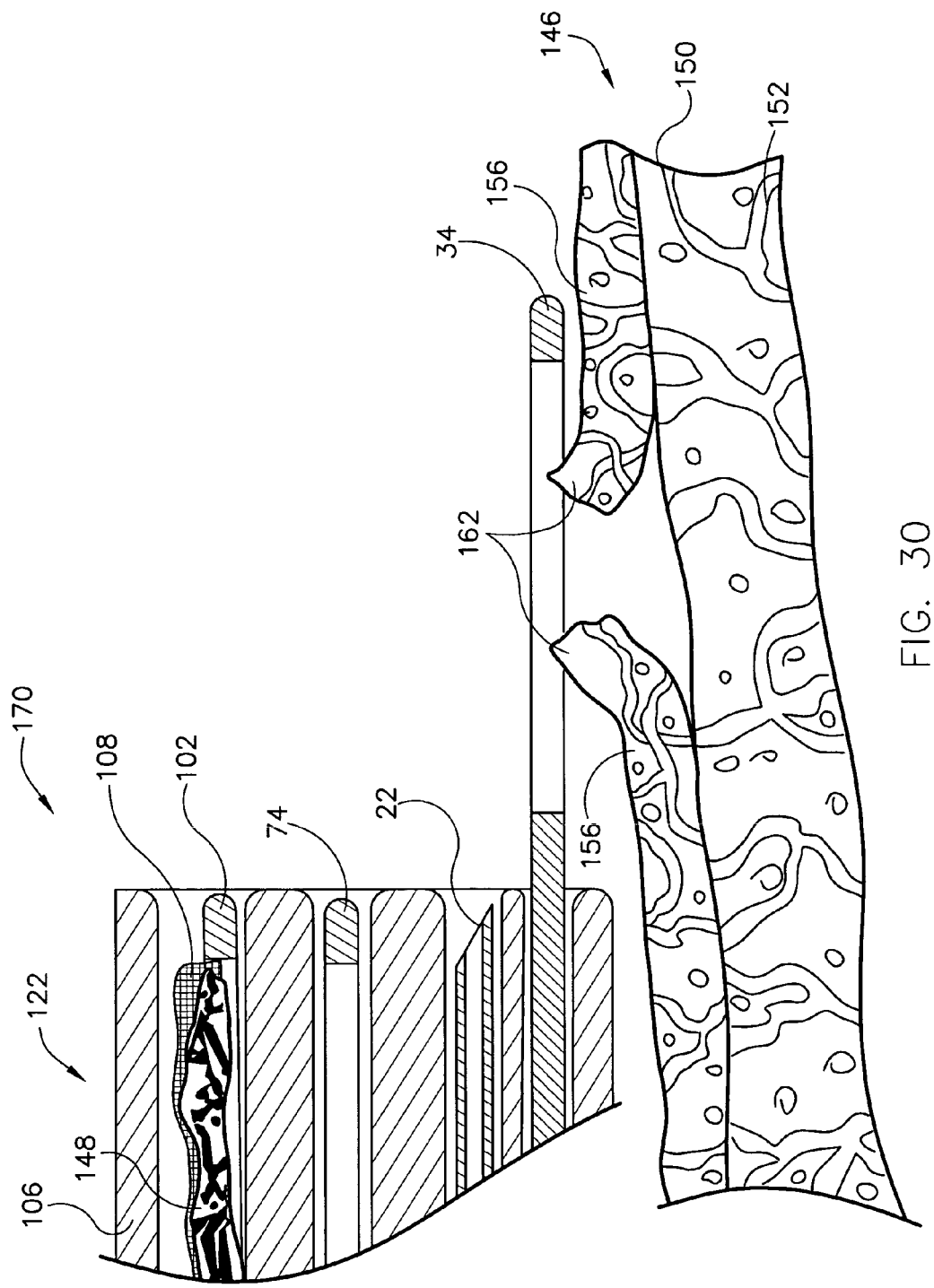
FIG. 30 is the cross section of FIG. 29 shown with the ablating loop directly contacting the edges of tissue remaining in the patient.

After removing the abnormal growth 148 from the patient 146, the user may desire to ablate at least the edges 162 of tissue 150 remaining in the patient. To ablate the edges 162 of tissue remaining in the patient 146, the user extends the ablating loop 34 and positions the loop 34 adjacent the edges 162, as shown in FIG. 29. Then, the user transfers energy from the ablating loop 34 to the edges 162 of tissue to ablate the edges 162. To increase the amount of energy transferred from the ablating loop 34 to the tissue 150, the ablating loop can be placed in direct contact with the tissue 150 adjacent the edges 162, as shown in FIG. 30.

By this local and accurate ablation method, diseased mucosal tissue 148 can be resected and removed from a patient for analysis and healthy adjacent mucosal tissue 156 and underlying muscular tissue 152 are substantially unharmed. Further, edges 162 of tissue 150 remaining in the patient 146 after the resection can be ablated through the application of energy thereto. The type of energizing may be of any conventional type, including the types mentioned above regarding energy source 30, such as radio frequency, electrical, and ultrasonic. Although this embodiment of a therapeutic method according to the present invention was described with reference to medical device 170, it will be appreciated by those skilled in the art that the method can be performed in a substantially similar manner using other disclosed embodiments without departing from the scope of the present invention. Further, the steps disclosed for using the device may be selectively performed, and in various order. For instance, although one embodiment includes a cutting step before an ablating step, a user can ablate before and/or after the cutting step.

Figure 31:
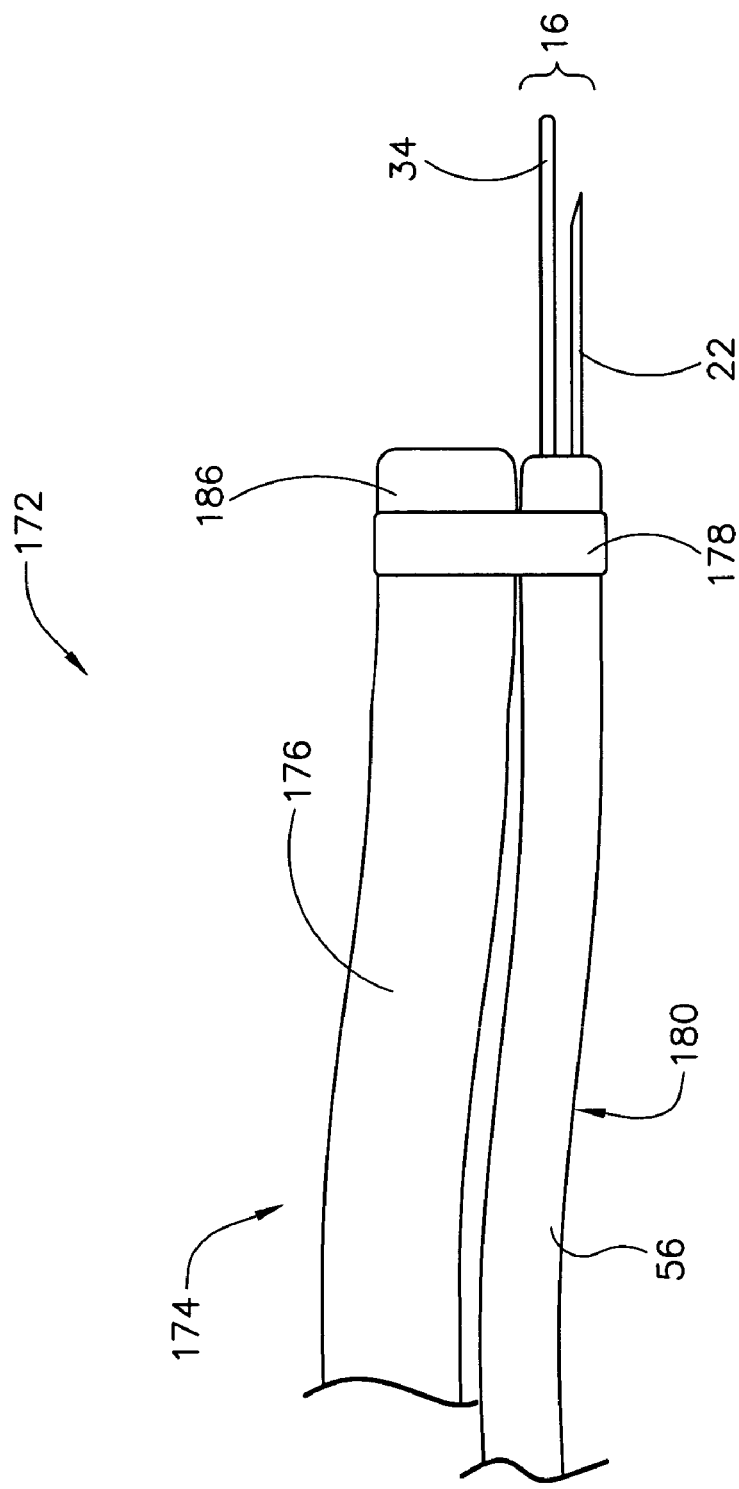
FIG. 31 is a perspective of the second embodiment of the device in combination with a conventional endoscope.
Figure 32:
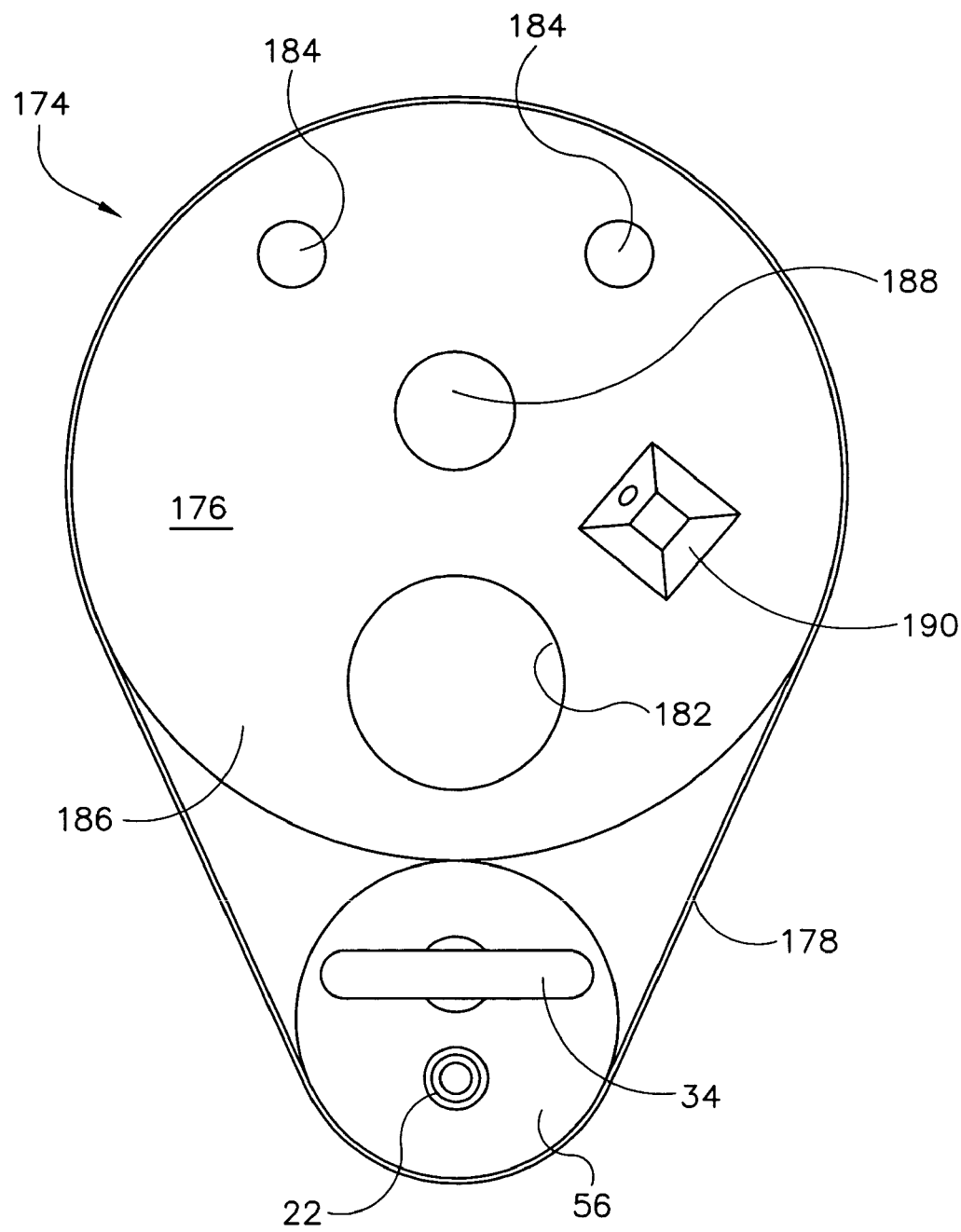
FIG. 32 is a front elevation of the combination shown in FIG. 31.

FIG. 31 shows an embodiment of a medical device 172 according to the present invention including an endoscope 174. In this embodiment, the probe 56 is connected to the exterior of the shaft 176 of endoscope 174. Although FIGS. 31 and 32 show a probe 56 according to the second embodiment of the present invention connected to the endoscope 174, other embodiments of the probe may be connected to the endoscope without departing from the scope of the present invention. Although the probe 56 may be connected to the endoscope 174 in other ways without departing from the scope of the present invention, in one embodiment the endoscope 174 is connected to the probe 56 by a flexible sleeve 178. Although the sleeve 178 may be made of other materials without departing from the scope of the present invention, in one embodiment the sleeve is made of rubber. In another embodiment, the probe 56 can be connected to the shaft 176 of the endoscope 174 by a rigid tube. In one embodiment, it is preferred that the probe 56 have a smooth exterior surface 180. One of the benefits of connecting the probe 56 to the exterior of the endoscope 174 is that the probe does not need to be sized to fit within the working channel 182 (shown in FIG. 32).

As shown in FIG. 32, the endoscope 174 can have a plurality of illuminators 184 for directing light toward an object (not shown) positioned adjacent the working end 186 of the shaft in a viewing area (not shown). The endoscope 174 can also have viewing optics 188 for viewing the object and a cleaning tab 190 for cleaning the optics. The medical device 172 and use thereof are otherwise the same as any of the earlier described embodiments, and therefore will not be described in further detail.

Although preferred uses of the medical device are to ablate and resect tissue in a patient, the device may also be used on materials other than tissue. In view of the above, it will be seen that the several objects of the invention are achieved.

When introducing elements of the present invention or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

What is claimed is:

1. A medical device for performing a therapeutic procedure on a patient comprising:
    an elongate probe extending to an applicator end sized and shaped to be slidably received in an endoscope working channel;
    an injection needle positioned adjacent the applicator end of the probe and communicatible with a fluid source for delivering fluid and an electrical energy source for delivering electrical energy to the needle when performing the therapeutic procedure on the patient, said needle having a central axis; and
    an ablating loop positioned adjacent the applicator end of the probe and communicatible with said electrical energy source for delivering electrical energy to the ablating loop when performing the therapeutic procedure, said ablating loop having a central axis that is spaced from the central axis of the injection needle;
    wherein during operation of the device, the injection needle and ablating loop have opposite charges for ablating tissue of the patient.

2. A medical device as set forth in claim 1 wherein the probe has a maximum width less than about three millimeters.

3. A medical device as set forth in claim 1 wherein the ablating loop includes a conductive mesh extending between opposite sides of the ablating loop.

4. A medical device as set forth in claim 1 wherein the injection needle is slidably disposed within the elongate probe such that the injection needle is movable from a stored position in which the needle is recessed within the probe and a deployed position in which the needle extends from the probe.

5. A medical device as set forth in claim 1 wherein the ablating loop is slidably disposed within the elongate probe such that the loop is movable from a stored position in which the loop is recessed within the probe and a deployed position in which the loop extends from the probe.

6. A medical device as set forth in claim 1 wherein the fluid source is a saline source for delivering saline to the injection needle.

7. A medical device as set forth in claim 1 wherein the electrical energy source is an ultrasonic electrical energy source for selectively delivering ultrasonic energy to the ablating loop and injection needle.

8. A medical device as set forth in claim 1 wherein the electrical energy source is a radio frequency electrical energy source for selectively delivering radio frequency energy to the ablating loop and injection needle.

9. A medical device as set forth in claim 8 wherein, during operation of the device, the charges on the injection needle and ablating loop change with time.

10. A medical device as set forth in claim 1 further comprising a cutting loop positioned adjacent the applicator end of the probe for cutting said tissue from the patient.

11. A medical device as set forth in claim 10 further comprising a retainer positioned adjacent the applicator end of the probe for capturing tissue removed from the patient by the cutting loop.

12. A medical device as set forth in claim 11 wherein the cutting loop and retainer are slidably disposed within the elongate probe such that the cutting loop and retainer are independently movable from relative stored positions in which the cutting loop and retainer are recessed within the probe and relative deployed positions in which the cutting loop and retainer extend from the probe.

13. A medical device for performing a therapeutic procedure on a patient comprising:
    an elongate endoscope extending to a working end, having optics for viewing an object positioned in a viewing area adjacent said working end, and having a working channel extending along the endoscope to a port adjacent the working end;
    an elongate probe slidably disposed in the working channel and having an applicator end corresponding to the working end of the endoscope;
    an injection needle positioned adjacent the applicator end of the probe in said viewing area and communicatible with a fluid source for delivering fluid to the needle and an electrical energy source for delivering electrical energy to the needle when performing the therapeutic procedure on the patient, said needle having a central axis; and
    an ablating loop positioned adjacent the applicator end of the probe in said viewing area and communicatible with the electrical energy source for delivering electrical energy to the ablating loop when performing the therapeutic procedure, said ablating loop having a central axis that is spaced from the central axis of the injection needle.

14. A medical device as set forth in claim 13 wherein, during operation of the device, the injection needle and ablating loop have opposite charges for ablating tissue of the patient.

15. A medical device as set forth in claim 14 wherein, during operation of the device, the charges of the injection needle and ablating loop change with time.

16. A medical device as set forth in claim 13 further comprising a cutting loop slidably disposed within the probe for cutting said tissue from the patient.

17. A medical device as set forth in claim 16 further comprising a retainer positioned adjacent the applicator end of the probe for capturing tissue removed from the patient by the cutting loop.

18. A method for performing a procedure on a patient comprising:
    guiding a working end of an endoscope to a predetermined location within the patient;
    positioning an ablating loop having a central axis and an injection needle having a central axis adjacent the working end of the endoscope such that the central axis of the ablating loop is spaced from the central axis of the injection needle;
    injecting fluid through the injection needle into tissue of the patient adjacent the predetermined location within the patient; and
    applying electrical energy to the injection needle and ablating loop simultaneously such that the injection needle and ablating loop have opposite charges, thereby ablating at least a portion of the tissue.

19. A method for performing a procedure as set forth in claim 18 wherein, in the step of applying electrical energy, the energy is applied such that the charges of the injection needle and ablating loop change with time.

20. A method for performing a procedure as set forth in claim 18 further comprising positioning a cutting loop adjacent said working end and cutting said portion of tissue from the patient using said cutting loop.

21. A method for performing a procedure as set forth in claim 20 further comprising positioning a retainer adjacent the working end and capturing the cut tissue with said retainer for removal from the patient.

22. A medical device for performing a therapeutic procedure on a patient comprising:

an elongate endoscope extending to a working end having an exterior surface and having optics for viewing an object positioned in a viewing area adjacent said working end;

an elongate probe connected to the exterior surface of the endoscope and having an applicator end corresponding to the working end of the endoscope;

an injection needle positioned adjacent the applicator end of the probe in said viewing area and communicatible with a fluid source for delivering fluid to the needle and an electrical energy source for delivering electrical energy to the needle when performing the therapeutic procedure on the patient; and an ablating loop positioned adjacent the applicator end of the probe in said viewing area and communicatible with the electrical energy source for delivering electrical energy to the ablating loop when performing the therapeutic procedure.

23. A method for performing a procedure on a patient comprising:

guiding a working end of an endoscope having an elongate probe connected to an exterior surface of the endoscope adjacent said working end to a predetermined location within the patient;

positioning an ablating loop and an injection needle adjacent an application end of the probe corresponding to the working end of the endoscope;

injecting fluid through the injection needle into tissue of the patient adjacent the predetermined location within the patient; and applying electrical energy to the injection needle and ablating loop simultaneously such that the injection needle and ablating loop have opposite charges, thereby ablating at least a portion of the tissue.

* * * * *